United States Patent
Tanaka

(10) Patent No.: US 10,376,161 B2
(45) Date of Patent: Aug. 13, 2019

(54) FINGER ARTERIAL DILATABILITY TESTING METHOD, FINGER ARTERIAL DILATABILITY TESTING DEVICE, AND FINGER ARTERIAL DILATABILITY TESTING PROGRAM

(71) Applicant: SAPPORO MEDICAL UNIVERSITY, Sapporo-shi, Hokkaido (JP)

(72) Inventor: Gohichi Tanaka, Sapporo (JP)

(73) Assignee: SAPPORO MEDICAL UNIVERSITY, Sapporo-shi, Hokkaido (JP)

( * ) Notice: Subject to any disclaimer, the term of this patent is extended or adjusted under 35 U.S.C. 154(b) by 945 days.

(21) Appl. No.: 14/431,626

(22) PCT Filed: Oct. 4, 2013

(86) PCT No.: PCT/JP2013/077103
§ 371 (c)(1),
(2) Date: Mar. 26, 2015

(87) PCT Pub. No.: WO2014/054788
PCT Pub. Date: Apr. 10, 2014

(65) Prior Publication Data
US 2015/0265166 A1    Sep. 24, 2015

(30) Foreign Application Priority Data
Oct. 4, 2012   (JP) .................................. 2012-222570

(51) Int. Cl.
*A61B 5/021*  (2006.01)
*A61B 5/02*   (2006.01)
(Continued)

(52) U.S. Cl.
CPC .......... *A61B 5/02116* (2013.01); *A61B 5/022* (2013.01); *A61B 5/02007* (2013.01);
(Continued)

(58) Field of Classification Search
CPC .............. A61B 5/02007; A61B 5/6826; A61B 5/02108
See application file for complete search history.

(56) References Cited

U.S. PATENT DOCUMENTS

| | | | |
|---|---|---|---|
| 4,597,393 A | 7/1986 | Yamakoshi et al. | |
| 5,379,774 A | 1/1995 | Nishimura et al. | |

(Continued)

FOREIGN PATENT DOCUMENTS

| | | | |
|---|---|---|---|
| JP | S59181129 A | 10/1984 | |
| JP | H06165764 A | 6/1994 | |

(Continued)

OTHER PUBLICATIONS

Tanaka et al. "A novel photoplethysmography technique to derive normalized arterial stiffness as a blood pressure independent measure in the finger vascular bed" Published Oct. 26, 2011 • 2011 Institute of Physics and Engineering in Medicine Physiological Measurement, vol. 32, No. 11.*

(Continued)

*Primary Examiner* — Patricia Mallari
*Assistant Examiner* — Michael Catina
(74) *Attorney, Agent, or Firm* — Muncy, Geissler, Olds & Lowe, P.C.

(57) ABSTRACT

[Problem] To provide a finger arterial dilatability testing method, finger arterial dilatability testing device, and finger arterial dilatability testing program with which it is possible to simply test for early signs of arteriosclerosis using the small vessels of the finger arteries.
[Solution] In the present invention, the following are provided: a pulse wave data storage step for storing the resting (Continued)

pulse wave data and the reperfusion pulse wave data after releasing occlusion at one forearm, for the arteries of each finger of both hands which are clamped using a predetermined sequence; an NPV calculation step for calculating, on the basis of the pulse wave data stored in the pulse wave data storage step, an NPV for each heartbeat, where the NPV is obtained by dividing the amplitude of the alternating current component of the pulse wave by the average direct current component value of each pulse wave; a pulse pressure data acquisition step for acquiring the pulse pressure which is obtained by subtracting the diastolic blood pressure from the systolic blood pressure; and an FCR ratio calculation step for calculating, on the basis of the pulse pressure acquired by the pulse pressure data acquisition step, for each heartbeat the index (FCR ratio) that shows the vasodilation reaction of the finger arteries.

15 Claims, 14 Drawing Sheets

(51) Int. Cl.
*A61B 5/022* (2006.01)
*A61B 5/00* (2006.01)
*A61B 5/0295* (2006.01)
*A61B 5/024* (2006.01)

(52) U.S. Cl.
CPC ........ *A61B 5/0295* (2013.01); *A61B 5/02108* (2013.01); *A61B 5/02241* (2013.01); *A61B 5/6826* (2013.01); *A61B 5/7225* (2013.01); *A61B 5/7264* (2013.01); *A61B 5/7278* (2013.01); *A61B 5/7282* (2013.01); *A61B 5/02416* (2013.01); *A61B 2560/0475* (2013.01)

(56) References Cited

U.S. PATENT DOCUMENTS 8,216,152 B2   7/2012  Tanaka et al.
2010/0004546 A1   1/2010  Tanaka et al.

FOREIGN PATENT DOCUMENTS

| JP | H10295655 A | 11/1998 |
| JP | 2010214021 A | 9/2010 |
| JP | 2011189080 A | 9/2011 |
| JP | 5039123 B2 | 10/2012 |
| WO | 2008105229 A1 | 9/2008 |

OTHER PUBLICATIONS

International Search Report of PCT/JP2013/077103 filed on Oct. 4, 2013 and a translation thereof.

* cited by examiner

[Fig.1]
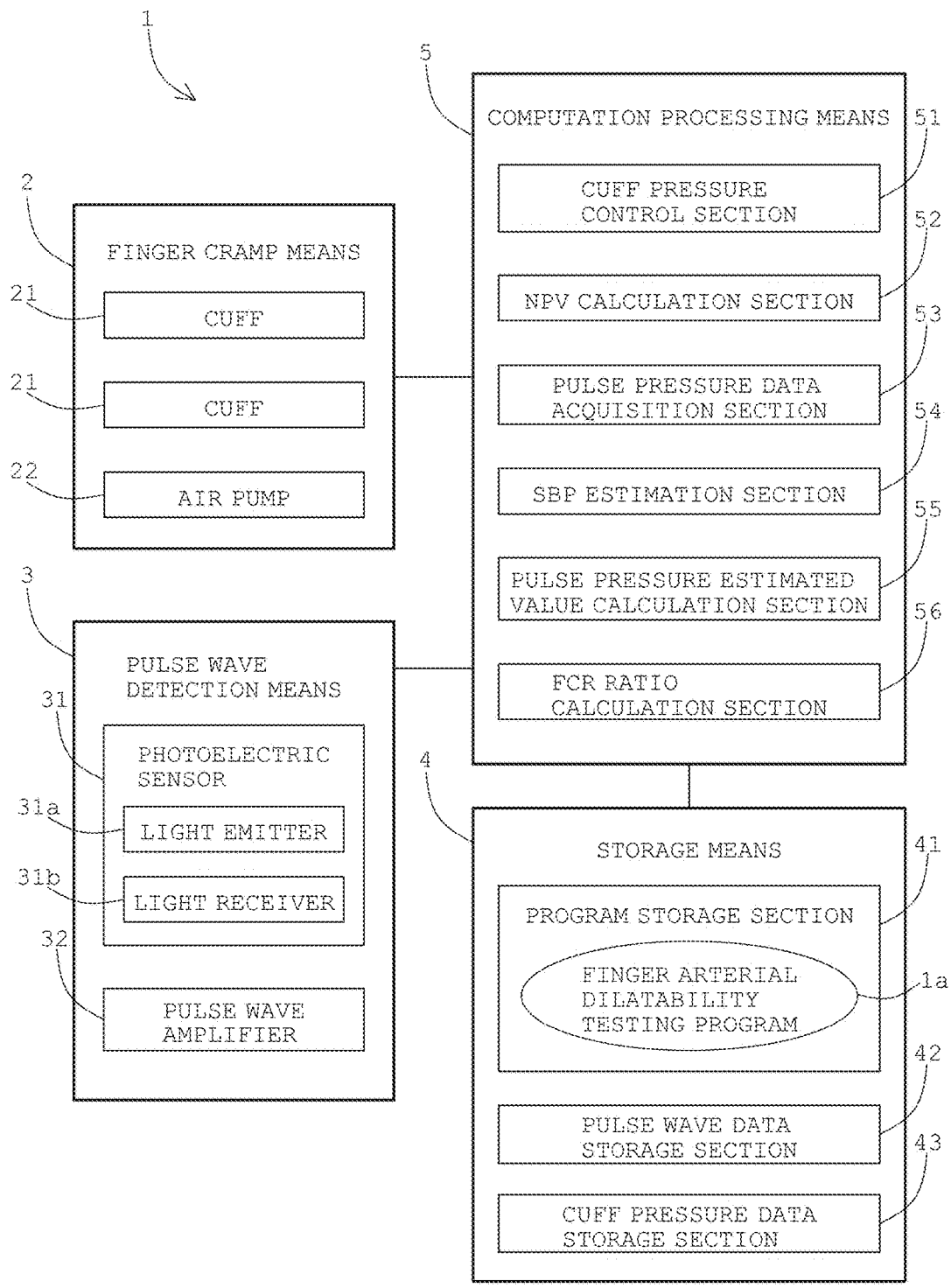

[Fig.2]
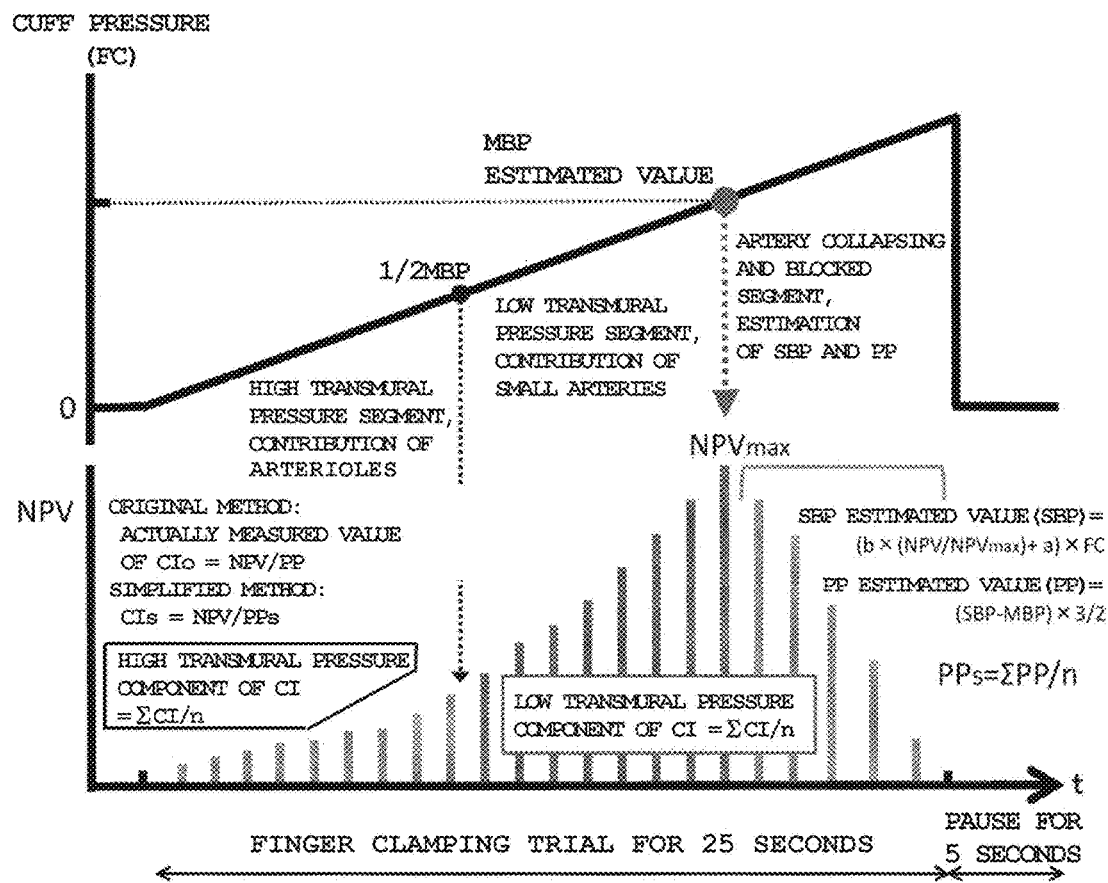

[Fig.3]

| COMPARISON ITEMS | RATIONALE | FCR METHOD | ENDO-PAT METHOD | |
|---|---|---|---|---|
| TARGET INDEX | VASCULAR ENDOTHELIAL FUNCTION: RELAXATION OF SMOOTH MUSCLE RESULTING FROM EFFECT OF NO →INCREASE IN COMPLIANCE(C) → INCREASE IN PULSATION VOLUME(ΔV) AND ENTIRE VASCULAR VOLUME(V) | C(DIRECT) ○ | ΔV(INDIRECT) △ | |
| INDEPENDENCE OF PULSE PRESSURE(ΔP) AS AN INFLUENTIAL FACTOR | ΔV=C×ΔP | ○ | × ↑WHEN ΔP↑ | (EXAMPLE 5) |
| INDEPENDENCE OF TRANSMURAL PRESSURE(Pt) AS AN INFLUENTIAL FACTOR | C=f(Pt) Pt=MEAN BLOOD PRESSURE(MBP)-CUFF PRESSURE(Pc) | ○ INDEPENDENT BECAUSE CUFF PRESSURE(Pc) GRADUALLY INCREASES AND AVERAGE OF C VALUES OVER ENTIRE RANGE OF Pt IS USED | × CHANGES WITH Pt AND C BECAUSE CUFF PRESSURE(Pc) IS FIXED | |
| INDEPENDENCE OF ARTERIAL STIFFNESS | STIFFNESS IS RESISTANCE FACTOR AGAINST VASODILATION | SIMULTANEOUS TEST USING FEI, STATISTICALLY ELIMINATE INFLUENCES | INMEASURABLE | |
| DEGREE OF COINCIDENCE | COINCIDE WITH EACH OTHER WHEN INFLUENCES OF PULSE PRESSURE, TRANSMURAL PRESSURE, AND STIFFNESS ARE REMOVED | AS EXPECTED (EXAMPLE 6) | | |

[Fig.4]
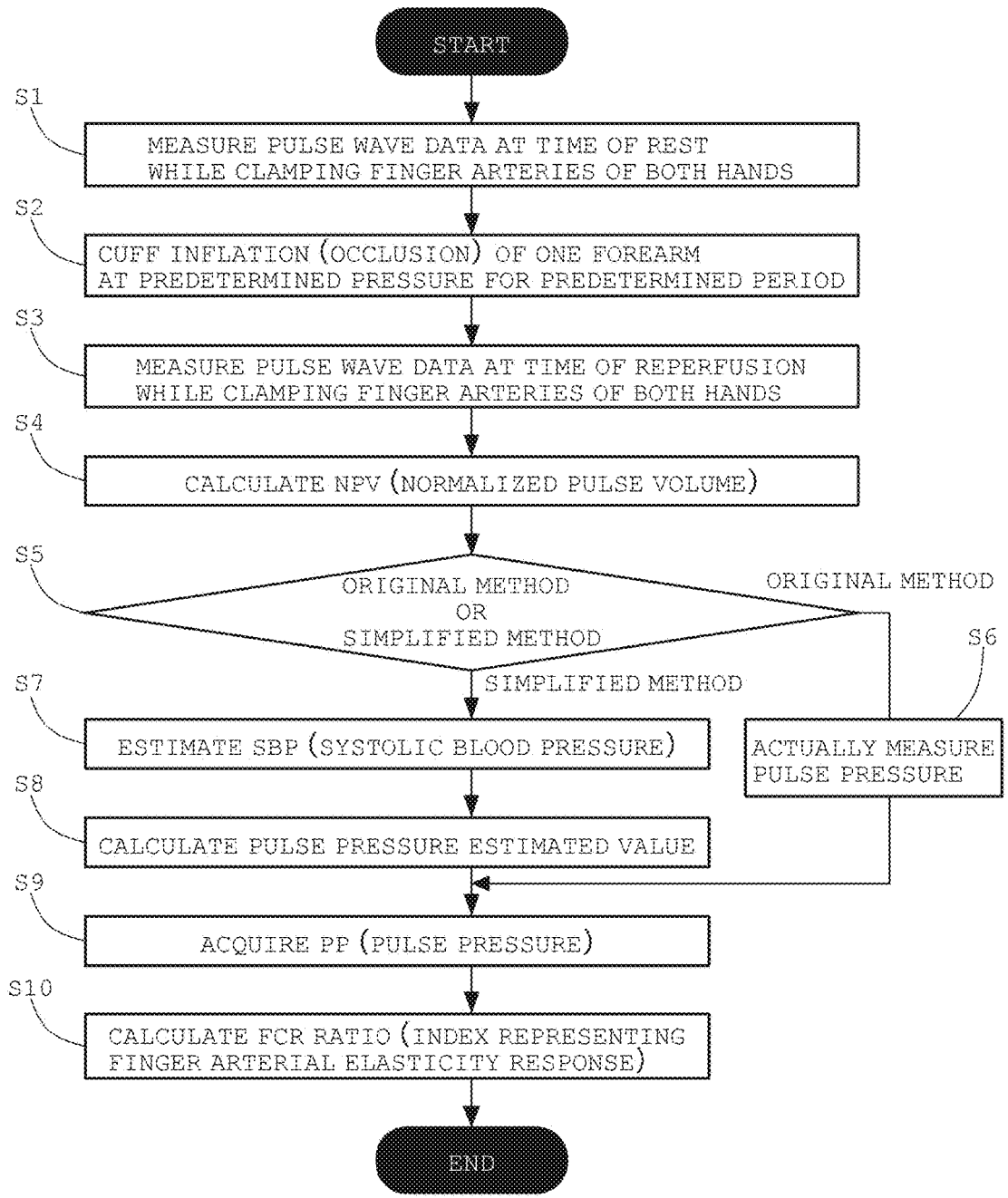

[Fig.5]

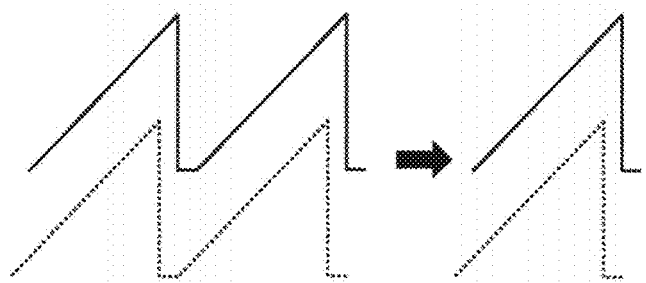

AT TIME OF REST:
6 MEASUREMENT TRIALS (3 MINUTES)
EVERY 30 SECONDS BEFORE OCCLUSION

HAND r ON OCCLUSION SIDE

CUFF INFLATION (OCCLUSION) AT SYSTOLIC BLOOD PRESSURE + 50mmHg FOR 5 MINUTES

HAND c ON CONTROL SIDE

NO OCCLUSION

AT TIME OF REPERFUSION:
6 TRIALS (3 MINUTES) EVERY 30 SECONDS

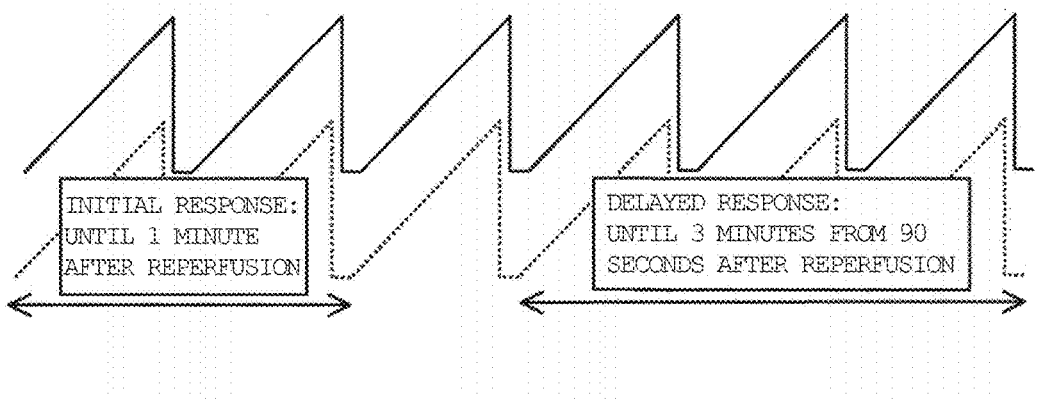

INITIAL RESPONSE: UNTIL 1 MINUTE AFTER REPERFUSION

DELAYED RESPONSE: UNTIL 3 MINUTES FROM 90 SECONDS AFTER REPERFUSION

[Fig.6]
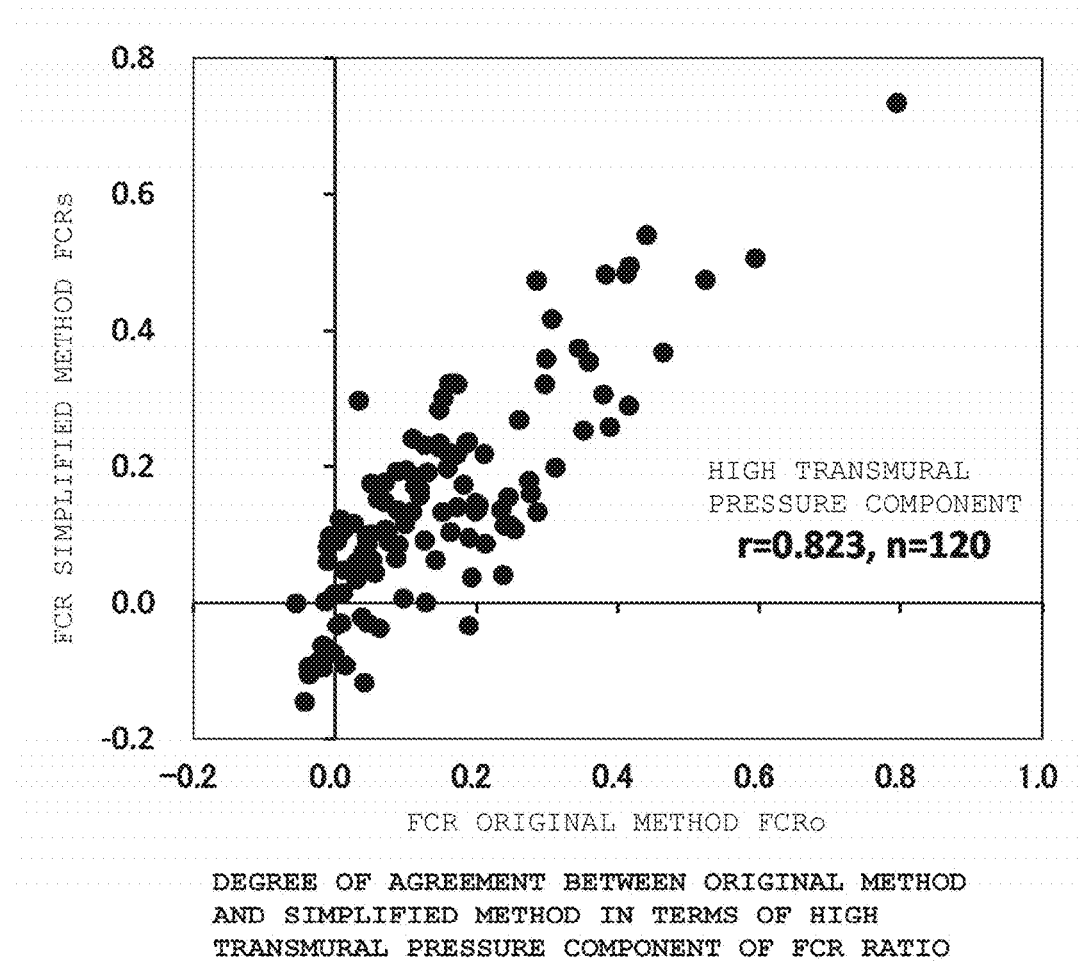
DEGREE OF AGREEMENT BETWEEN ORIGINAL METHOD AND SIMPLIFIED METHOD IN TERMS OF HIGH TRANSMURAL PRESSURE COMPONENT OF FCR RATIO

[Fig.7]
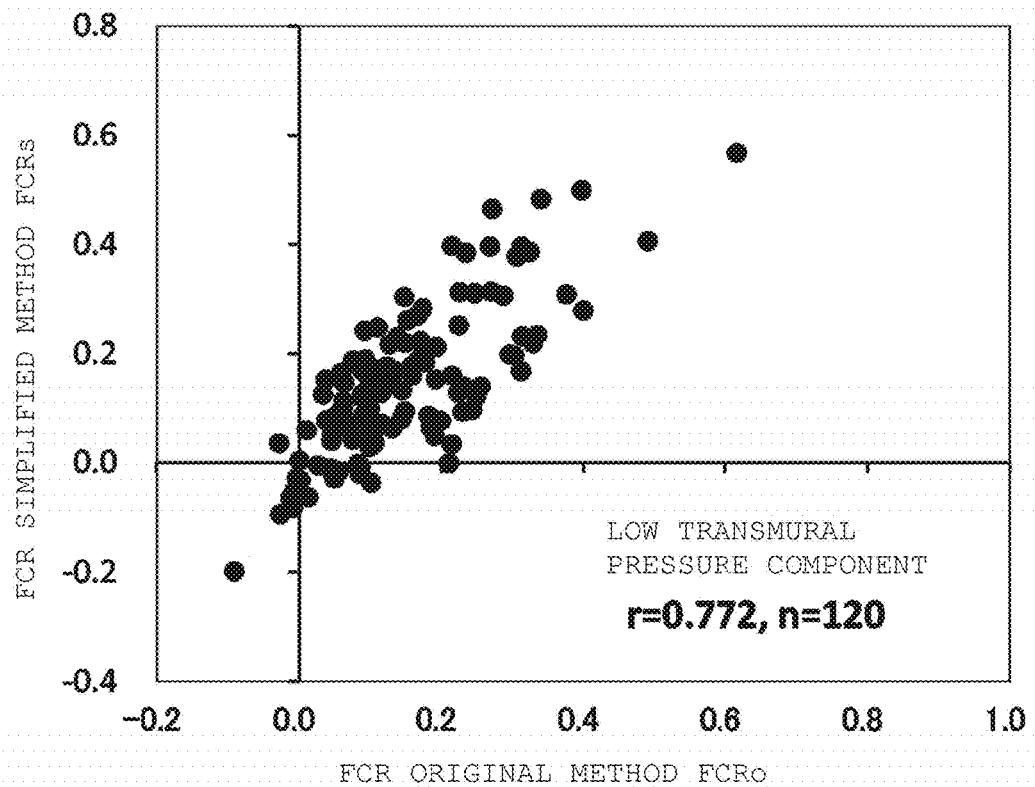
DEGREE OF AGREEMENT BETWEEN ORIGINAL METHOD
AND SIMPLIFIED METHOD IN TERMS OF LOW
TRANSMURAL PRESSURE COMPONENT OF FCR RATIO

[Fig.8]
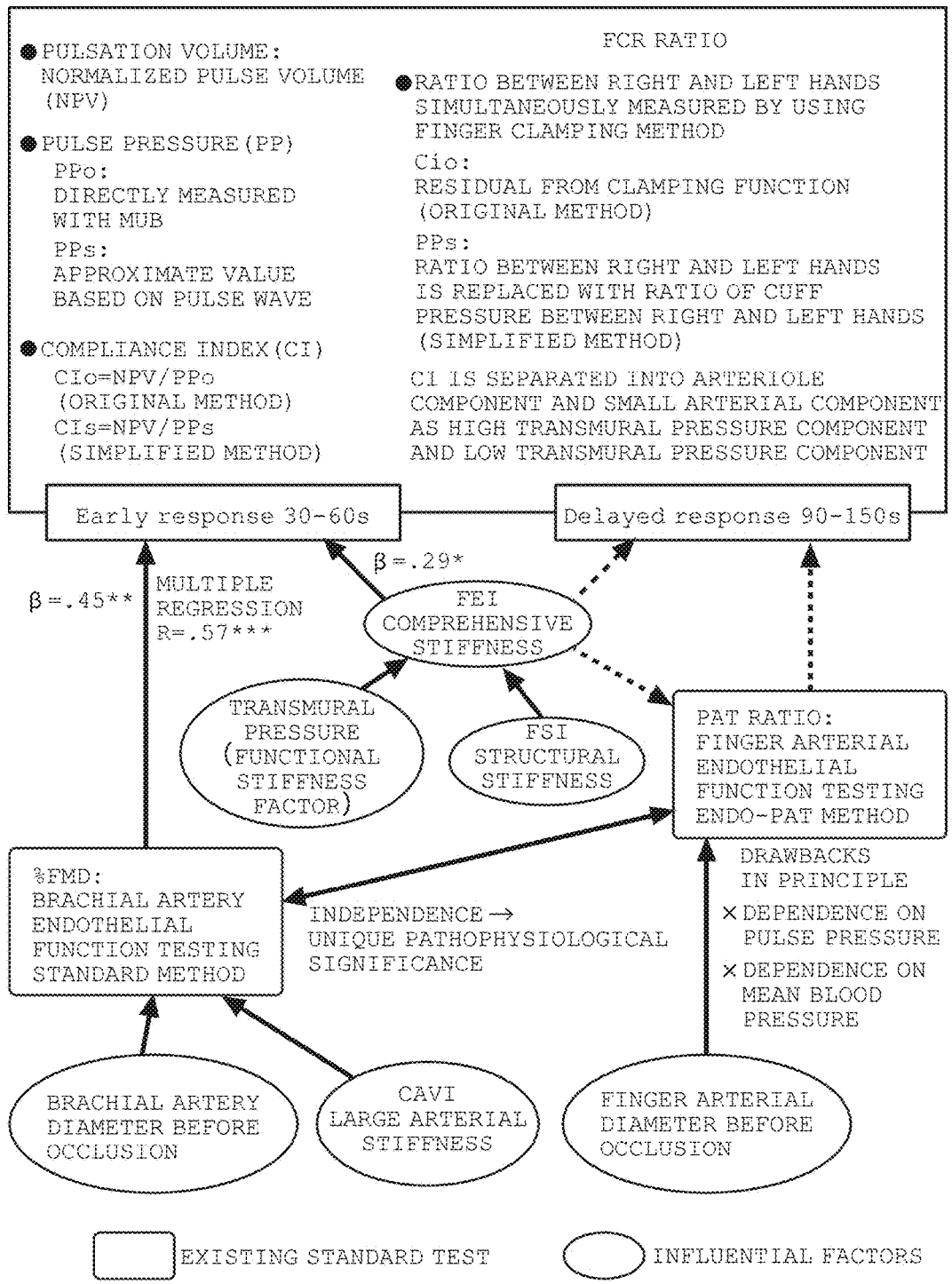

[Fig.9]
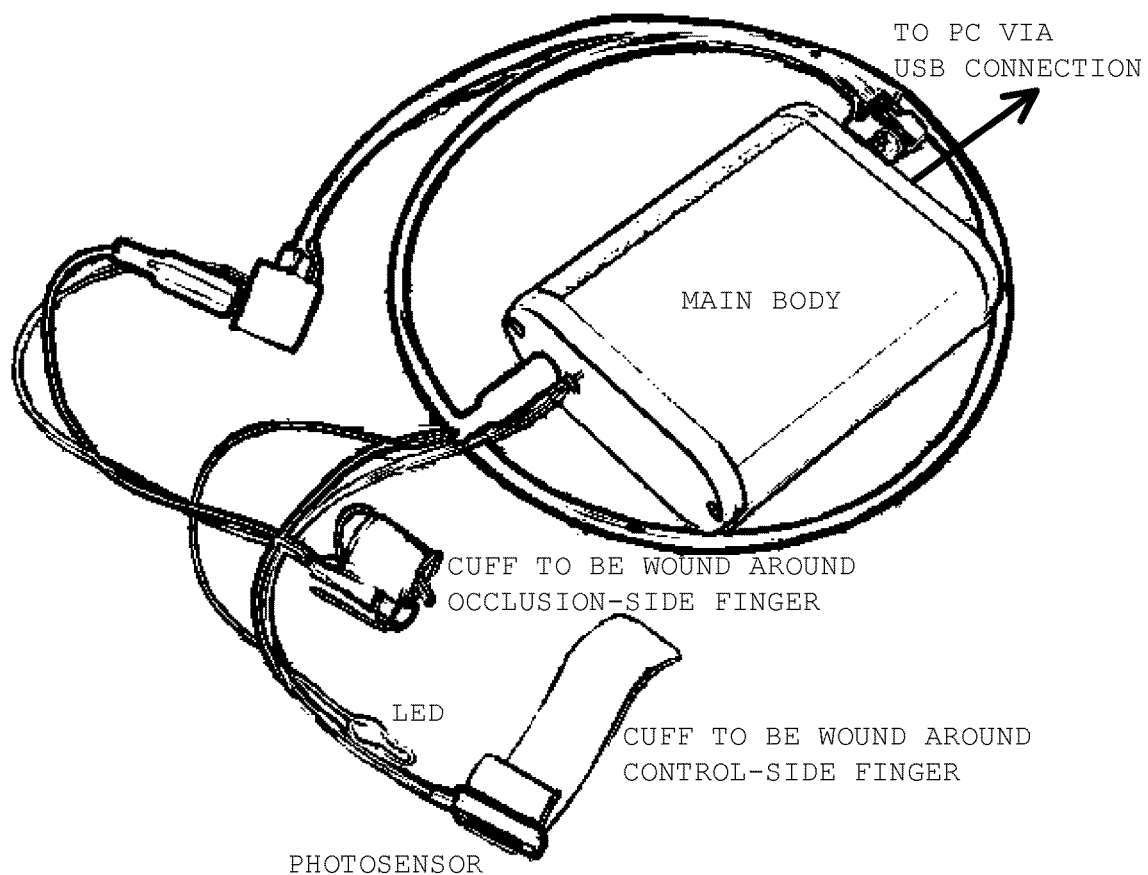

[Fig.10]
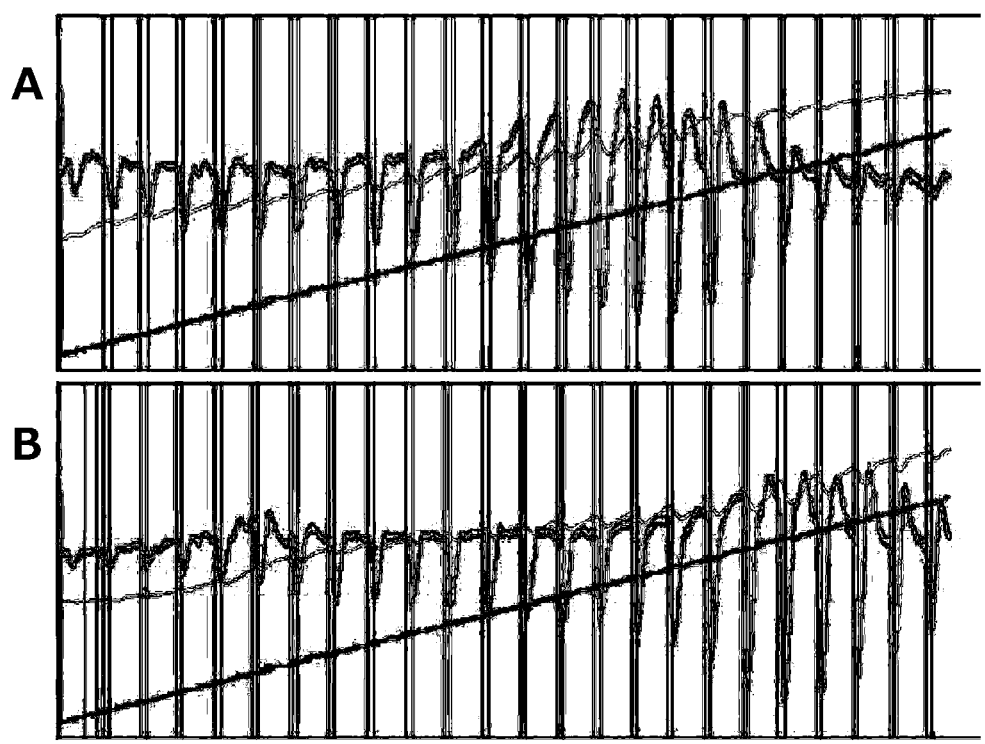

[Fig.11A]
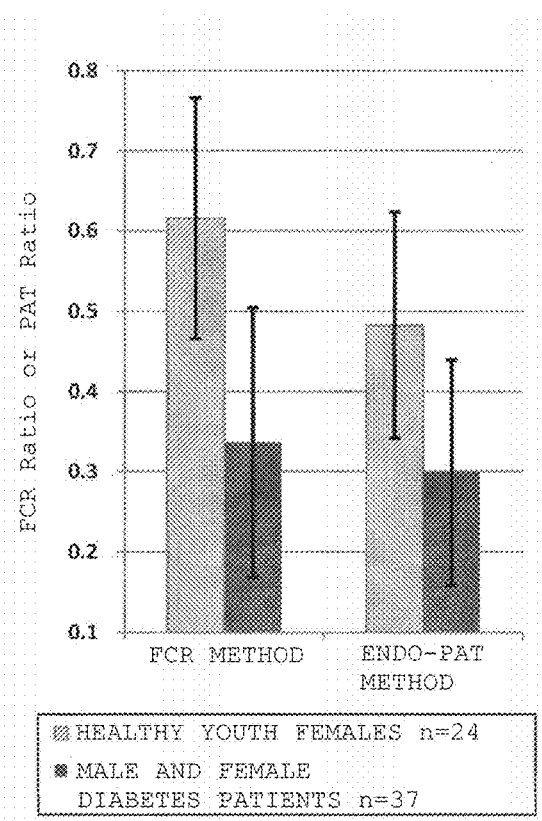
[Fig.11B]
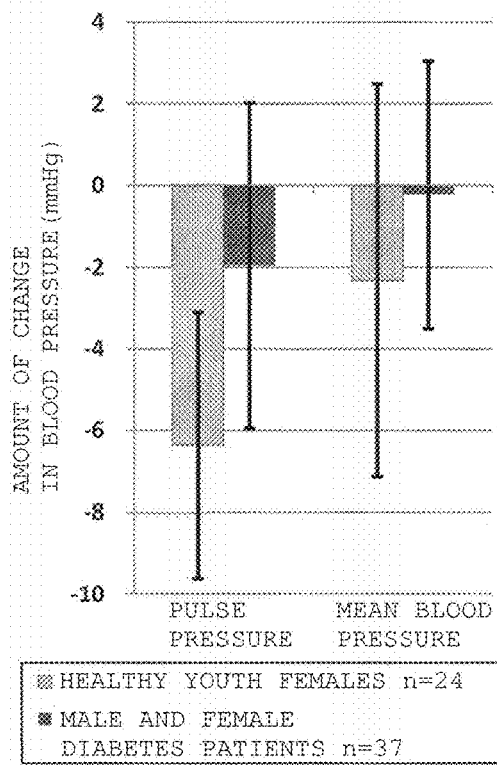

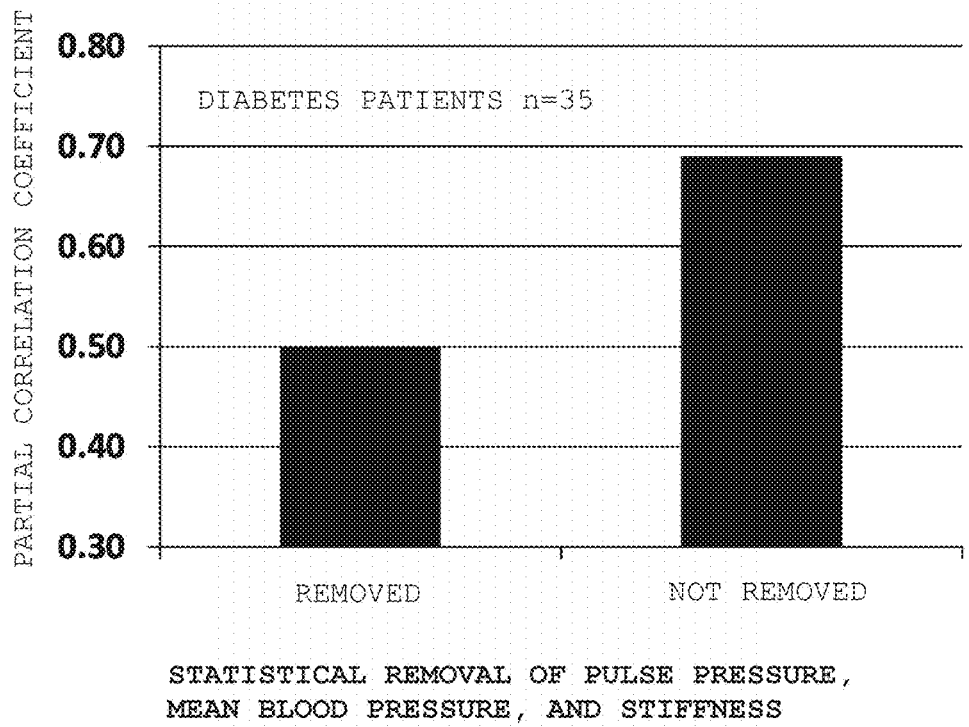
[Fig.12]

[Fig.13A]
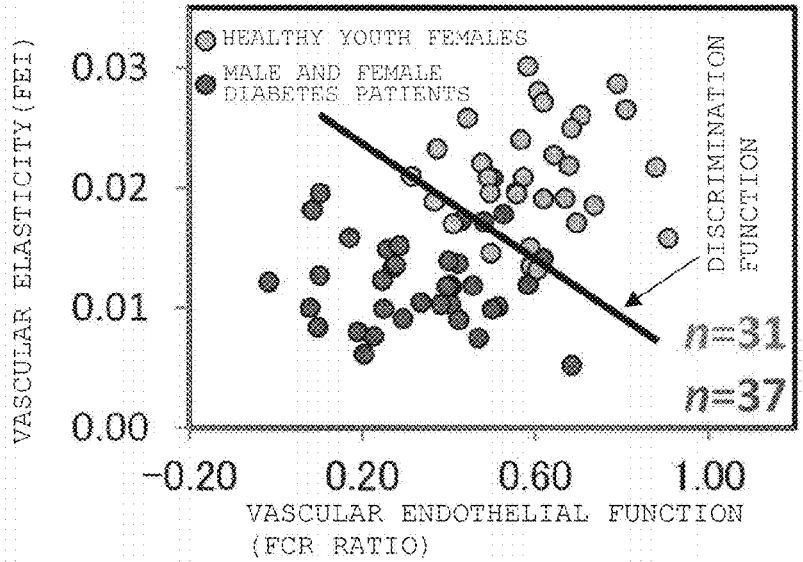
[Fig.13B]
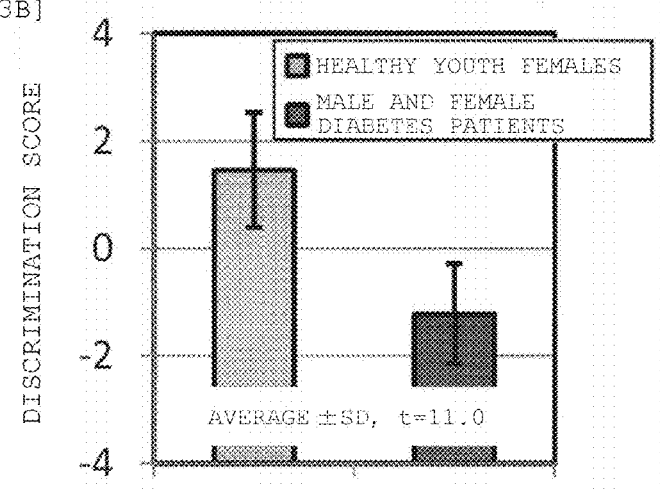
[Fig.13C]
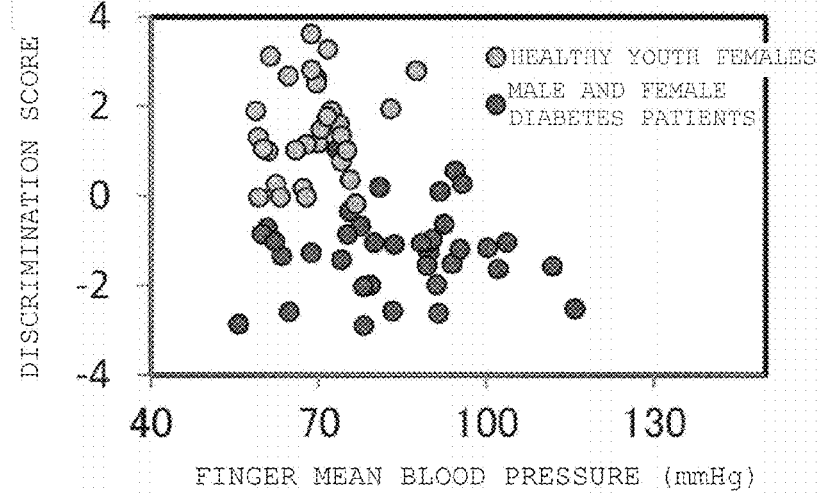

[Fig.14A]

DISCRIMINATION USING ONLY FCR RATIO

|  | DISCRIMINATIVE PREDICTION | | | |
|---|---|---|---|---|
| OBSERVATION | HEALTHY YOUTH FEMALES | DIABETES PATIENTS | TOTAL | %CORRECT CLASSIFICATION |
| HEALTHY YOUTH FEMALES | 29 | 10 | 39 | SPECIFICITY 74.4 |
| DIABETES PATIENTS | 11 | 38 | 49 | SENSITIVITY 77.6 |
| TOTAL | 40 | 48 | 88 | |
| %CORRECT PREDICTION | 72.5 | 79.2 | | PREDICTIVE VALUE =76.1% |

[Fig.14B]

DISCRIMINATION USING FCR RATIO AND FEI

|  | DISCRIMINATIVE PREDICTION | | | |
|---|---|---|---|---|
| OBSERVATION | HEALTHY YOUTH FEMALES | DIABETES PATIENTS | TOTAL | %CORRECT CLASSIFICATION |
| HEALTHY YOUTH FEMALES | 33 | 6 | 39 | SPECIFICITY 84.6 |
| DIABETES PATIENTS | 6 | 43 | 49 | SENSITIVITY 87.8 |
| TOTAL | 39 | 49 | 88 | |
| %CORRECT PREDICTION | 84.6 | 87.8 | | PREDICTIVE VALUE =86.4% |

[Fig.14C]

DISCRIMINATION USING FCR RATIO, FEI, AND FINGER MEAN BLOOD PRESSURE

|  | DISCRIMINATIVE PREDICTION | | | |
|---|---|---|---|---|
| OBSERVATION | HEALTHY YOUTH FEMALES | DIABETES PATIENTS | TOTAL | %CORRECT CLASSIFICATION |
| HEALTHY YOUTH FEMALES | 37 | 2 | 39 | SPECIFICITY 94.9 |
| DIABETES PATIENTS | 2 | 47 | 49 | SENSITIVITY 95.9 |
| TOTAL | 39 | 49 | 88 | |
| %CORRECT PREDICTION | 94.9 | 95.9 | | PREDICTIVE VALUE =95.5% |

FINGER ARTERIAL DILATABILITY TESTING METHOD, FINGER ARTERIAL DILATABILITY TESTING DEVICE, AND FINGER ARTERIAL DILATABILITY TESTING PROGRAM

CROSS REFERENCE TO RELATED APPLICATIONS

This application is a national stage of International Application No.: PCT/JP2013/077103, which was filed on Oct. 4, 2013, and which claims priority to JP 2012-222570 which was filed on Oct. 4, 2012, and which are both herein incorporated by reference.

TECHNICAL FIELD

The present invention relates to a finger arterial dilatability testing method, a finger arterial dilatability testing device, and a finger arterial dilatability testing program that are suitable for a test for early signs of arteriosclerosis in the small vessels of the finger arteries.

BACKGROUND ART

The vascular endothelial function, which fails in the earliest period of arteriosclerosis, is expected in recent years to be used to diagnose cardiovascular diseases, diabetes, and other lifestyle diseases in their preclinical stages. In the most standard testing method used in worldwide clinical sites (flow-mediated dilation: FMD method), after a forearm is occluded for five minutes, the occlusion is removed to cause reactive hyperemia. An ultrasonic diagnosis device is then used to measure a flow-mediated dilation response, the intensity of which is maximized about one minute after reperfusion, to find a maximum increase ratio (% FMD) of the diameter of the brachial artery.

Further, evaluation of an increase in pulsation amplitude in reactive hyperemia (PAT ratio) by using a finger plethysmogram (evaluation of delay response after 90 seconds, which is a point of time later than post-reperfusion initial response assessed by using FMD method), is called peripheral artery tonometry testing (Endo-PAT method) which has been commercially available in Israel and increasingly used in clinical applications.

Further, as a device using the finger plethysmogram, there has been a proposed vascular endothelial function evaluation system including evaluation means for evaluating a vascular endothelial function level based on the difference between a pulse wave peak value and a pulse wave base value, evaluation means for evaluating the vascular endothelial function level based on the proportions of a reflected wave component (AI) to the systolic blood pressure of the pulse wave before occlusion of a forearm and after resumption of blood flow, evaluation means for evaluating the vascular endothelial function level by using a vascular aging index (AG) as a pulse wave characteristic value of the acceleration pulse wave, or any other means (Patent Literature 1).

CITATION LIST

Patent Literature

Patent Literature 1: Japanese Patent Application Laid-Open No. 2011-189080

SUMMARY OF INVENTION

Technical Problem

However, according to a physiological theory stating that arteriosclerosis across the body starts from small vessels, the FMD method described above, which is directed to the brachial artery, which is a large blood vessel, as an evaluation target, is not necessarily suitable to detect sings of arteriosclerosis in the earliest stage. Further, an ultrasonic diagnosis device necessary for the measurement of a flow-mediated dilation response is undesirably expensive, and moreover, image analysis of a result of the measurement tends to be subjective and requires a skill of a tester.

Further, in the Endo-PAT method described above, although the amplitude of the pulsation in the finger arteries is clearly influenced by both the structural stiffness (intrinsic stiffness) of finger blood vessels under testing and the blood pressure at the time of testing, no consideration of the influences is undesirably given at all. Moreover, it has been widely accepted that the delay response (response 90 to 150 seconds after reperfusion), which is an evaluation target of the Endo-PAT method, and then initial response (response 30 to 60 seconds after reperfusion), which is an evaluation target of the FMD method described above, poorly correlate with each other and each of the two methods has its own pathophysiological significance and clinical significance.

Further, since the invention described in Patent Literature 1 relates to analysis of the waveform of a composite pulse wave combined with a reflected wave and is hence restricted by complicated influence factors associated with the reflection, physiological interpretation of a result of the analysis is undesirably very difficult. Moreover, in Patent Literature 1, external pressure applied to a finger is not changed during the testing but is fixed at a constant value determined by pre-measurement before the occlusion at the arm as an optimum pressure. As a result, when the blood pressure after the reperfusion greatly changes as compared with the blood pressure at the time of rest, it cannot be said that the pressure predetermined at the time of rest is an optimum pressure, undesirably resulting in inaccurate evaluation.

The present invention has been made to solve the problems described above. An object of the present invention is to provide a finger arterial dilatability testing method, a finger arteriolar dilatability testing device, and a finger arterial dilatability testing program that allow a simple test for early signs of arteriosclerosis in the small vessels of the finger arteries.

Solution to Problem

A finger arterial dilatability testing method according to the present invention is a finger arterial dilatability testing method for testing a vasodilation response of finger arteries and comprises: a pulse wave data storage step of storing, for each of the finger arteries of both hands that are cramped in accordance with a predetermined sequence, pulse wave data at the time of rest and pulse wave data at the time of reperfusion after one forearm is occluded; an NPV calculation step of calculating, on the basis of the pulse wave data stored in the pulse wave data storage step, a normalized pulse volume (NPV), which is obtained by dividing the amplitude of an AC component of a pulse wave by the average of a DC component of the pulse wave, for each heartbeat; a pulse pressure data acquisition step of acquiring pulse pressure (PP), which is obtained by subtracting a diastolic blood pressure from a systolic blood pressure; and an FCR ratio calculation step of calculating an index representing a vasodilation response of the finger arteries (FCR ratio) for each heartbeat, the FCR ratio being the ratio between compliance indices for both hands at the time of reperfusion normalized by the ratio between the compliance indices for both hands at the time of rest, the compliance index being an index obtained by dividing the normalized pulse volume (NPV) calculated in the NPV calculation step by the pulse pressure (PP) acquired in the pulse pressure data acquisition step.

As an aspect of the present invention, in the FCR ratio calculation step, the normalization may be performed by dividing the ratio between the compliance indices for both hands at the time of reperfusion by the ratio between the compliance indices for both hands at the time of rest.

As another aspect of the present invention, the FCR ratio may be expressed by the following Expression (1):

$$\text{FCR ratio}=[ln(CI_r/CI_c)]_y-[ln(CI_r/CI_c)]_x \qquad \text{Expression (1)}$$

where CI: compliance index (=NPV/PP),
r: subscript indicating hand that undergoes forearm occlusion,
c: subscript indicating hand that undergoes no occlusion,
x: subscript indicating the time of rest, and
y: subscript indicating the time of reperfusion.

As another aspect of the present invention, the method may further comprise:

a cuff pressure data storage step of storing cuff pressure applied by a cuff that clamps each of the finger arteries; an SBP estimation step of calculating systolic blood pressure values (SBPt) at points of time t after the NPV is maximized by using the following Expression (2) and averaging the calculated systolic blood pressure values to derive an systolic blood pressure (SBP):

$$SBPt=(b \times (NPVt/NPVmax)+a) \times FCt \qquad \text{Expression (2)}$$

where NPVt: NPV at time t,
NPVmax: maximum NPV,
FCt: cuff pressure (FC) at time t, and
a, b: constant; and a pulse pressure estimated value calculation step of calculating a pulse pressure estimated value (PPs) by using the following Expression (3) based on the systolic blood pressure (SBP) estimated in the SBP estimation step:

$$PPs=(SBP-MBP) \times 3/2 \qquad \text{Expression (3)}$$

where MBP (mean blood pressure): cuff pressure at the time when NPV is maximized, and
in the pulse pressure data acquisition step, the pulse pressure estimated value calculated in the pulse pressure estimated value calculation step may be acquired as the pulse pressure.

As another aspect of the present invention, the method may further comprise a discrimination function calculation step of calculating a discrimination function in the form of a multiple regression equation using a numerical target variable showing whether a person under discrimination belongs to a healthy group or a diabetes group based on group of data having two variables, a finger arterial elasticity index (FEI), which is a linear regression slope (n) of the following Expression (4), and the FCR ratio:

$$ln(NPV)=ln(bn)-n \cdot Pr \qquad \text{Expression (4)}$$

where b: constant, and
Pr: relative cuff pressure (difference between the cuff pressure at the time when the amplitude of the pulse wave is maximized and each cuff pressure);

a discrimination score calculation step of substituting the FEI and the FCR ratio of the person under discrimination into the discrimination function to calculate a discrimination score; and a diabetes discrimination step of determining whether the person under discrimination belongs to the healthy group or the diabetes group based on the discrimination score.

A finger arterial dilatability testing device according to the present invention is a finger arterial dilatability testing device for testing a vasodilation response of finger arteries and includes a pulse wave data storage section that stores, for each of the finger arteries of both hands that are cramped in accordance with a predetermined sequence, pulse wave data at the time of rest and pulse wave data at the time of reperfusion after one forearm is occluded; an NPV calculation section that calculates, on the basis of the pulse wave data stored in the pulse wave data storage section, a normalized pulse volume (NPV), which is obtained by dividing the amplitude of an AC component of a pulse wave by the average of a DC component of the pulse wave, for each heartbeat; a pulse pressure data acquisition section that acquires pulse pressure (PP), which is obtained by subtracting diastolic blood pressure from systolic blood pressure; and an FCR ratio calculation section that calculates an index representing a vasodilation response of the finger arteries (FCR ratio) for each heartbeat, the FCR ratio being the ratio between compliance indices for both hands at the time of reperfusion normalized by the ratio between the compliance indices for both hands at the time of rest, the compliance index being an index obtained by dividing the normalized pulse volume (NPV) calculated by the NPV calculation section by the pulse pressure (PP) acquired by the pulse pressure data acquisition section. Further, a finger arterial dilatability testing program according to the present invention causes a computer to function as the constituent sections described above.

As an aspect of the present invention, the FCR ratio calculation section may perform the normalization by dividing the ratio between the compliance indices for both hands at the time of reperfusion by the ratio between the compliance indices for both hands at the time of rest.

As another aspect of the present invention, the FCR ratio may be expressed by the following Expression (1):

$$\text{FCR ratio}=[ln(CI_r/CI_c)]_y-[ln(CI_r/CI_c)]_x \qquad \text{Expression (1)}$$

where CI: compliance index (=NPV/PP),
r: subscript indicating hand that undergoes forearm occlusion,
c: subscript indicating hand that undergoes no occlusion,
x: subscript indicating the time of rest, and
y: subscript indicating the time of reperfusion.

As another aspect of the present invention, the finger arterial dilatability testing device may further comprise: a cuff pressure data storage section that stores cuff pressure applied by a cuff that clamps each of the finger arteries; an SBP estimation section that calculates maximum blood pressure values (SBPt) at points of time t after the NPV is maximized by using the following Expression (2) and averages the calculated systolic blood pressure values to derive an estimated systolic blood pressure (SBP):

$$SBPt=(b \times (NPVt/NPVmax)+a) \times FCt \qquad \text{Expression (2)}$$

where NPVt: NPV at time t,
NPVmax: maximum NPV,
FCt: cuff pressure (FC) at time t, and
a, b: constant; and a pulse pressure estimated value calculation section that calculates a pulse pressure estimated value (PPs) by using the following Expression (3) based on the systolic blood pressure (SBP) estimated by the SBP estimation section:

$$PPs=(SBP-MBP)\times 3/2 \qquad \text{Expression (3)}$$

where MBP (mean blood pressure): cuff pressure at the time when NPV is maximized, or a computer is caused to function as the constituent section described above, and the pulse pressure data acquisition section may acquire the pulse pressure estimated value calculated by the pulse pressure estimated value calculation section as the pulse pressure.

As another aspect of the present invention, the finger arterial dilatability testing device may further comprise: a discrimination function calculation section that calculates a discrimination function in the form of a multiple regression equation using a numerical target variable showing whether a person under discrimination belongs to a healthy group or a diabetes group based on group of data having two variables, a finger arterial elasticity index (FEI), which is a linear regression slope (n) of the following Expression (4), and the FCR ratio:

$$ln(NPV)=ln(bn)-n\cdot Pr \qquad \text{Expression (4)}$$

where b: constant, and

Pr: relative cuff pressure (difference between the cuff pressure at the time when the amplitude of the pulse wave is maximized and each cuff pressure);

a discrimination score calculation section that substitutes the FEI and the FCR ratio of the person under discrimination into the discrimination function to calculate a discrimination score; and a diabetes discrimination section that determines whether the person under discrimination belongs to the healthy group or the diabetes group based on the discrimination score, or a computer may be caused to function as the constituent sections described above.

ADVANTAGEOUS EFFECTS OF INVENTION

According to the present invention, early signs of arteriosclerosis in the arterioles of the finger arteries can be readily tested.

BRIEF DESCRIPTION OF DRAWINGS

FIG. 1 is a block diagram showing an embodiment of a finger arterial dilatability testing device and a finger arterial dilatability testing program according to the present embodiment.

FIG. 2 is a graph showing the relationship of the cuff pressure and NPV versus time course in a case where clamping trials are performed in accordance with a sequence according to the present embodiment.

FIG. 3 is a table showing comparison results between an FCR method described above according to the present invention and an Endo-PAT method of related art.

FIG. 4 is a flowchart showing an embodiment of a finger arterial dilatability testing method according to the present invention.

FIG. 5 shows a measurement protocol in the present embodiment.

FIG. 6 is a graph showing the degree of agreement of a high transmural pressure component between an original method and a simplified method in Example 2.

FIG. 7 is a graph showing the degree of agreement of a low transmural pressure component between the original method and the simplified method in Example 2.

FIG. 8 shows experimental results in Example 3.

FIG. 9 is a photograph showing the exterior appearance of a prototype device in Example 4.

FIG. 10 shows a waveform monitor screen during measurement using prototype software in Example 4.

FIG. 11 In Example 5, FIG. 11(a) is a graph showing experimental results, and FIG. 11(b) is graph showing the amounts of change in the pulse pressure and the mean blood pressure.

FIG. 12 is a graph showing experimental results in Example 6.

FIG. 13 In Example 7, FIG. 13(a) is a graph showing the relationship between an FCR ratio and FEI, FIG. 13(b) is a graph showing average discrimination scores, and FIG. 13(c) is a graph showing the relationship between the discrimination score and the finger mean blood pressure.

FIG. 14 In Example 9, FIG. 14(a) shows results representing a diabetes patient discrimination predictive value in a case where only the FCR ratio is used, FIG. 14(b) shows results in a case where FEI is used as well as the FCR ratio, and FIG. 14(c) shows results in a case where a finger mean blood pressure is used as well as the FCR ratio and FEI.

DESCRIPTION OF EMBODIMENTS

A finger arterial dilatability testing method, a finger arterial dilatability testing device, and a finger arterial dilatability testing program (hereinafter collectively referred to as FCR (Finger arterial Compliance Response test) method in some cases) according to the present invention are suitable for calculation of an FCR (Finger arterial Compliance Response: vasodilation response of finger arteries) ratio, which has been proposed by the present inventor and is a novel index for evaluating early sings of arteriosclerosis in the small vessels of the finger arteries.

An embodiment of the finger arterial dilatability testing method, the finger arterial dilatability testing device, and the finger arterial dilatability testing program according to the present invention will be described below with reference to the drawings.

As shown in FIG. 1, a finger arterial dilatability testing device 1 according to the present embodiment is formed primarily of finger cramp means 2 for cramping a finger, pulse wave detection means 3 for detecting a pulse wave, storage means 4 for storing a finger arterial dilatability testing program 1a according to the present embodiment and a variety of data, and computation processing means 5 for controlling the constituent means described above and acquiring the variety of data for computation processing. Each of the constituent means will be described below in detail.

The finger clamp means 2 clamps the finger arteries of a subject at a desired pressure value. In the present embodiment, the finger cramp means 2 includes a pair of cuffs 21, 21, which are wound around a finger with the aid of a hook and loop fastener in a detachable manner, and an air pump 22, which delivers air into the cuffs 21, 21. In the present embodiment, the cuffs 21, 21 are attached to the index fingers of both hands and cramp the finger arteries. The air pump 22 is automatically controlled by a cuff pressure control section 51, which will be described later, and causes the finger arteries in both hands to be clamped in accordance with a predetermined sequence. A hook and loop fastener is not necessarily used to attach and detach the finger clamp means 2 and may be replaced with another attachment and detachment means.

The pulse wave detection means 3 detects a volume pulse wave representing a change in volume of the finger arteries. In the present embodiment, the pulse wave detection means 3 includes a photoelectric sensor 31, which detects the amount of light, and a pulse wave amplifier 32, which amplifies an output signal from the photoelectric sensor 31 and outputs the amplified signal as pulse wave data. In the present embodiment, photoelectric volume pulse wave data (FPG) is, but not necessarily, detected as the pulse wave data.

The photoelectric sensor 31 includes a light emitter 31*a*, such as an LED (Light Emitting Diode), which is fixed to the nail of the finger, and a light receiver 31*b*, such as a photodiode, which is disposed on the ball side of the finger and in a position facing the light emitter 31*a*, and the light receiver 31*b* detects the amount of light emitted from the light emitter 31*a* and passing through the finger. The pulse wave amplifier 32 outputs the amplified pulse wave data to a pulse wave data storage section 42, which will be described later.

In the present embodiment, each of the cuffs 21 is integrated with the light receiver 31*b* and is fixed to the finger by placing the light receiver 31*b* on the ball of the finger, winding the cuff 21 around the finger with the light emitter 31*a* fixed to the nail of the finger, and fastening the entire structure with the hook and loop fastener or any other component. It is therefore unnecessary to provide a plurality of cuffs 21 having different diameters, but one type of cuff 21 allows optimum attachment in accordance with the finger diameter of each of a plurality of subjects. Further, the light emitter 31*a* and the light receiver 31*b* are allowed to come into intimate contact with the finger, whereby the amount of shift of the optical path in the time course of the finger cramping can be minimized.

The storage means 4 stores a variety of data and functions as a working area where the computation processing means 5 carries out a computation processing. In the present embodiment, the storage means 4 is formed, for example, of a hard disk, a ROM (Read Only Memory), a RAM (Random Access Memory), and a flash memory and includes a program storage section 41, which stores the finger arterial dilatability testing program 1*a* according to the present embodiment, a pulse wave data storage section 42, and a cuff pressure data storage section 43, as shown in FIG. 1.

The program storage section 41 has the finger arterial dilatability testing program 1*a* according to the present embodiment installed therein. The finger arterial dilatability testing program 1*a*, when executed by the computation processing means 5, allows a computer to function as constituent sections described later. The finger arterial dilatability testing program 1*a* is not necessarily used as described above. For example, the finger arterial dilatability testing program 1*a* may be stored in a computer readable recording medium, such as a CD-ROM and a DVD-ROM, and may by directly read from the recording medium. The finger arterial dilatability testing program 1*a* may instead be read from an external server or any other component that operates in an ASP (Application Service Provider) method or a cloud computing method.

The pulse wave data storage section 42 stores pulse wave data detected by the pulse wave detection means 3. In the present embodiment, the pulse wave data storage section 42 stores, the following pulse wave data on the finger arteries in each of both hands cramped by the finger cramp means 2 in accordance with the predetermined sequence: pulse wave data at the time of rest; and separate pulse wave data at the time of reperfusion after the forearm of one of the hands is occluded at predetermined pressure for a predetermined period.

The cuff pressure data storage section 43 stores data on the cuff pressure at which the cuffs 21 clamp the finger arteries. In the present embodiment, the cuff pressure data storage section 43 stores the cuff pressure applied by the cuffs 21, 21, which are attached to both hands, both at the time of rest and at the time of reperfusion.

The computation processing means 5 is formed, for example, of a CPU (Central Processing Unit) and executes the finger arterial dilatability testing program 1*a*, which causes the computation processing means 5 to function as a cuff pressure control section 51, an NPV calculation section 52, a pulse pressure data acquisition section 53, an SBP estimation section 54, a pulse pressure estimated value calculation section 55, and an FCR ratio calculation section 56. Each of the constituent sections will be described below in more detail.

The cuff pressure control section 51 automatically controls the air pump 22 to arbitrarily adjust the cuff pressure applied by the cuffs 21, 21. In the present embodiment, the cuff pressure control section 51 automatically controls the finger cramp means 2 in such a way that a sequence of trial action including increasing the cuff pressure from zero at a fixed rate for 25 seconds including the time when the amplitude of the pulse wave is maximized and eliminating the cramping for five seconds before the cuff pressure returns to zero is repeated six times (for three minutes in total). In the present embodiment, the cuff pressure control section 51 keeps acquiring cuff pressure data and stores them in the cuff pressure data storage section 43.

The NPV calculation section 52 calculates a normalized pulse volume (NPV=$\Delta$I/I), which is directly proportional to the amplitude of the pulse wave. The amount of transmitted light corresponding to a change in pulsation ($\Delta$I) is determined by the amplitude of the AC component of the pulse wave. The amount of light that the finger (tissue and blood) (I) allows to transmit is determined by the average of the DC component of the pulse wave at the same point of time when $\Delta$I is determined. The NPV calculation section 52 therefore calculates the normalized pulse volume (NPV) for each heartbeat by dividing the amplitude of the AC component of the pulse wave at a certain point of time by the average of the DC component of the pulse wave at the same point of time based on the pulse wave data stored in the pulse wave data storage section 42.

The pulse pressure data acquisition section 53 acquires pulse pressure (PP) obtained by subtracting diastolic blood pressure (DBP) from systolic blood pressure (SBP). In the present embodiment, the pulse pressure data acquisition section 53 may instead acquire actually measured pulse pressure as the pulse pressure. In this case, the actually measured pulse pressure can be acquired, for example, with a continuous hemomanometer (model MUB manufactured by Medisens, INC.), which is capable of measuring the blood pressure in the finger arteries by using a volume compensation method.

The continuous hemomanometer described above is, however, large and expensive and can be purchased for experiment and research purposes, but it is difficult to purchase the continuous hemomanometer, for example, in a typical hospital. Further, even if the continuous hemomanometer can be purchased and used for the measurement, the number of continuous hemomanometers is limited and the measurement period per person is long, which prevents simultaneous measurement, for example, in a medical examination of a large number of persons. The introduction of the continuous hemomanometer is therefore undesirably impractical.

In view of the fact described above, in the present embodiment, the pulse pressure data acquisition section 53 may instead acquire the pulse pressure in the form of a pulse pressure estimated value (PPs) estimated from the pulse wave, which will be described later in detail. In the following description, an FCR method using an actually measured pulse pressure is called an "original method," and an FCR method using a pulse pressure estimated value is called a "simplified method."

A method for estimating the pulse pressure in the FCR method according to the present embodiment will be described below in comparison with a typical oscillometric method. In general, to measure the blood pressure, a cuff (manchette) is wound around a forearm, and air is delivered into the cuff to cramp the blood vessels to temporarily block the blood flow. When the cramping is then gradually eliminated, the blood pressure eventually exceeds the pressure applied by the cuff that cramps the blood vessels. The blood thus starts flowing intermittently in response to the beats of the heart.

In the oscillometric method, after the cuff pressurization and during the pressure reduction, the blood pressure is determined by checking the change in the cuff pressure that reflects vibration of the vascular wall (pressure pulse wave) synchronized with the beats of the heart. In general, it is believed that the cuff pressure measured when the pressure pulse wave steeply increases is considered as the systolic blood pressure and the cuff pressure measured when the pressure pulse wave is steeply decreases is considered as the diastolic blood pressure.

FIG. 2 shows the relationship of the cuff pressure and NPV versus time course in a case where the finger blood vessels are instead clamped and measured in accordance with the sequence described above in a pressure increase procedure in place of the pressure reduction procedure described above. In a typical oscillometric method, the mean blood pressure (MBP) is measured when the cuff pressure maximizes the amplitude of the pulse wave, and systolic blood pressure (SBP) is measured when the cuff pressure steeply lowers the amplitude of the pulse wave. It is noted that NPV shown in FIG. 2 is directly proportional to the amplitude of the pulse wave. In this method, however, since the mean blood pressure (MBP) and systolic blood pressure (SBP) are determined one at a time at points of time temporally separate from each other by several seconds, the pulse pressure to be estimated is greatly influenced by variation in blood pressure during the several seconds.

In view of the fact described above, as shown in FIG. 2, for several heartbeats after the time when the mean blood pressure (MBP) is determined but before the pulse completely vanishes, systolic blood pressure (SBP) is estimated for each heartbeat based on the ratio of the amplitude of the pulse wave of the heartbeat to the maximum amplitude of the pulse wave, and the average of the values of systolic blood pressure is set as systolic blood pressure (SBP). This procedure allows determination of averaged systolic blood pressure (SBP) at a point of time closer to the point of time when the mean blood pressure (MBP) is determined, whereby a combination of mean blood pressure (MBP), systolic blood pressure (SBP), and a pulse pressure estimated value (PPs) with reduced influence of the blood pressure variation described above can be obtained.

As shown in FIG. 2, in one sequence described above, since a segment from the time zero to the time when the cuff pressure reaches one-half the mean blood pressure (MBP) is a segment having high transmural pressure (mean blood pressure—cuff pressure), it can be said that the segment is a region where arterioles and small arteries slightly thicker than arterioles contribute to blood pressure. On the other hand, since a segment from the time when the cuff pressure reaches one-half the mean blood pressure (MBP) to the time when the cuff pressure reaches the mean blood pressure (MBP) is a segment having low transmural pressure (mean blood pressure—cuff pressure) and arterioles are collapsed, it can be said that the segment is a region where the small arteries primarily contribute to the blood pressure.

In the above description, the SBP estimation section 54 estimates the systolic blood pressure (SBP) necessary for calculation of the pulse pressure estimated value (PPs). Specifically, the SBP estimation section 54 acquires NPV calculated by the NPV calculation section 52, detects the time when NPV is maximized, and acquires the cuff pressure (FCt) at points of time t after the time when NPV is maximized from the cuff pressure data storage section 43. The SBP estimation section 54 then calculates the systolic blood pressure (SBPt) at the points of time t after NPV is maximized by using the following Expression (2) and averages the values of the systolic blood pressure (SBPt) to derive an estimated systolic blood pressure (SBP):

$$SBPt = (b \times (NPVt/NPVmax) + a) \times FCt \qquad \text{Expression (2)}$$

where NPVt: NPV at time t,
NPVmax: maximum NPV,
FCt: cuff pressure (FC) at time t, and
a, b: constant.

The pulse pressure estimated value calculation section 55 calculates the pulse pressure estimated value (PPs) based on the systolic blood pressure (SBP) estimated by the SBP estimation section 54. Specifically, the pulse pressure estimated value calculation section 55 acquires the mean blood pressure (MBP) in the form of the cuff pressure at the point of time when NPV is maximized from the cuff pressure data storage section 43, acquires the systolic blood pressure (SBP) estimated by the SBP estimation section 54, and calculates the pulse pressure estimated value (PPs) by using the following Expression (3):

$$PPs = (SBP - MBP) \times 3/2 \qquad \text{Expression (3)}$$

where MBP (mean blood pressure): cuff pressure at the time when NPV is maximized.

The FCR ratio calculation section 56 calculates an index representing a vasodilation response from finger arteries (FCR ratio). The inventor of the present application has defined the FCR ratio by using the following Expression (1) in order to aim for an increase in arterial compliance in the finger arteries at the time of reactive hyperemia and simultaneously assess the influences of effective pressure acting on the blood vessels (transmural pressure) at the time of the reactive hyperemia and the stiffness specific to the blood vessels in the finger under testing:

$$\text{FCR ratio} = [ln(CIr/CIc)]y - [ln(CIr/CIc)]x \qquad \text{Expression (1)}$$

where CI: compliance index (=NPV/PP),
r: subscript indicating hand that undergoes forearm occlusion,
c: subscript indicating hand that undergoes no occlusion,
x: subscript indicating the time of rest, and
y: subscript indicating the time of reperfusion.

The reason why the finger small arteries are aimed at instead of brachial artery or any other large arteries is to allow the present invention to be suitable not only for the physiological theory stating that arteriosclerosis across the body starts from small vessels but also for clinical diagnosis of microvascular diseases, such as diabetes and high blood pressure and to be applied to earliest diagnosis of these diseases.

In view of the above description, the FCR ratio calculation section 56 is configured to calculate the index representing a vasodilation response (FCR ratio) from the finger arteries for each heartbeat by using Expression (1) described above based on the normalized pulse volume (NPV) calculated by the NPV calculation section 52 and the pulse pressure (PP) acquired by the pulse pressure data acquisition section 53.

Further, as described above, in the original method according to the FCR method in the present embodiment, the pulse pressure data acquisition section 53 acquires the pulse pressure in the form of actually measured pulse pressure, and the FCR ratio calculation section 56 calculates the FCR ratio by using the actually measured value. On the other hand, in the simplified method according to the FCR method in the present embodiment, the pulse pressure data acquisition section 53 acquires the pulse pressure in the form of the pulse pressure estimated value calculated by the pulse pressure estimated value calculation section 55, and the FCR ratio calculation section 56 calculates the FCR ratio by using the pulse pressure estimated value.

In Expression (1) described above, CI is a finger arterial compliance index obtained by dividing NPV by PP, as described above. Further, in Expression (1) described above, the second term on the right side is a difference between the right and left hands that is permanently present between the compliance indices for the right and left hands and measured at the time of rest before the forearm occlusion in the FCR method.

That is, the FCR ratio is obtained by normalizing the ratio between the compliance indices, which are obtained by dividing NPV by PP, for both hands at the time of reperfusion by the ratio between the compliance indices for both hands at the time of rest. In the present embodiment, the normalization is performed by dividing the ratio between the compliance indices for both hands at the time of reperfusion by the ratio between the compliance indices for both hands at the time of rest. In Expression (1) described above, in which the ratios are expressed in the form of natural logarithm, the normalization is expressed in the form of subtraction. The normalization method is not limited to the method described above, and any method that allows normalization based on the ratio between the compliance indices for both hands at the time of rest may be selected as appropriate.

Further, Expression (1) described above can be expressed by the following Expression (5), whereas the Endo-PAT method gives no consideration on the pulse pressure expressed by the following Expression (5):

$$\text{FCR ratio} = [ln(NPVr/NPVc)]y - [ln(NPVr/NPVc)]x - ([ln(PPr/PPc)]y - [ln(PPr/PPc)]x) \quad \text{Expression (5)}$$

In a preliminary experiment conducted by the inventor of the present application, since the pulse pressure markedly decreases until one minute elapses after the reperfusion (that is, decrease in PPr and increase in compensatory PPc), the Endo-PAT method does not allow evaluation of an initial response until one minute and thirty seconds elapse after the reperfusion. The limitation is believed to be the reason why the PAT ratio in the Endo-PAT method is directed to the average of responses from one minute thirty seconds to three minutes after the reperfusion, that is, a reactive hyperemia delayed response as an evaluation target as shown in FIG. 2.

It is noted that also in the Endo-PAT method, the PAT ratio obtained by normalizing the ratio between the amplitude of the pressure pulse wave on the occlusion side and the amplitude of the pressure pulse wave on the control side by the ratio at the time of rest is calculated in order to remove the influence of the sympathetic nerve tonus on bilaterality, as in the case shown by Expression (5). It can therefore be said that a method for measuring the pulse wave simultaneously from finger arteries in both hands and calculating the cuff pressure bilateral ratio (FCr/FCc) provides novel means for estimating the pulse pressure bilateral ratio (PPr/PPc) based only on the pulse wave and the cuff pressure as well as the advantageous effect of removal of the influence of the sympathetic nerve tonus in the Endo-PAT method.

Although the Endo-PAT method also evaluates activation of the vascular endothelial function, but the evaluation is based on "relaxation of vascular smooth muscle resulting from stimulus made by NO (nitrogen monoxide) secreted from vascular endothelium," which has been proved by the largest amount of academic evidence. However, the PAT ratio in the Endo-PAT method is obtained by normalizing the ratio between the amplitude of the pressure pulse wave on the occluded side and the amplitude of the pressure pulse wave on the control side by the ratio at the time of rest, as described above. That is, the PAT ratio only allows evaluation of an indirect effect (secondary phenomenon) resulting from relaxed blood vessels. In contrast, in the FCR method according to the present invention, a target index is compliance corresponding to elasticity of blood vessels, and it can be said that that the FCR method allows direct evaluation of relaxation of vascular smooth muscle based on an increase in the compliance.

Further, under the circumstances in which the pulse pressure ($\Delta P$) and the transmural pressure (mean blood pressure—cuff pressure) are primary causes that influence the evaluation of the vascular endothelial function, the pulsation volume ($\Delta V$), which is a target index in the Endo-PAT method and obtained by multiplying the compliance by the pulse pressure, undesirably increases as the pulse pressure increases. Moreover, in the Endo-PAT method, since the cuff pressure is fixed, the transmural pressure undesirably changes as the mean blood pressure changes, and since the compliance is also a function of the transmural pressure, the pulsation volume ($\Delta V$), which is the target index, undesirably changes depending on the transmural pressure and the compliance. That is, the pulsation volume ($\Delta V$), which is the target index in the Endo-PAT method, is not independent of the pulse pressure and the transmural pressure, which are influential factors.

In contrast, in the FCR method, in which the compliance is the target index, the influence of the pulse pressure is eliminated. Further, as described above, the compliance is a function of the transmural pressure, but the average of compliance values measured over the entire range of the transmural pressure is used, whereby there is no influence of the transmural pressure. The FCR method is therefore independent of the pulse pressure and the transmural pressure, which are influential factors, and it can be said that the FCR method is theoretically superior to the Endo-PAT method.

Another cause that influences the evaluation of the vascular endothelial function is the arterial stiffness, which is a resistance factor against vascular dilation. In this regard, the FCR method measures the arterial volume that increases with the compliance that increases due to relaxation of vascular smooth muscle, whereas the Endo-PAT method cannot measure the arterial volume. Further, even when hard blood vessels are under measurement, a finger arterial elasticity index FEI (Japanese Patent No. 5,039,123), which has been uniquely developed by the inventor of the present application, can be measured immediately before the FCR method is performed, and the FEI allows correction of the influence of the stiffness. It can therefore be said that the FCR method, which is independent of arterial stiffness, which is an influential factor, is superior to the Endo-PAT method.

The arterial volume and the compliance are in theory expected to increase simultaneously. In this regard, the FCR method allows measurement of both the arterial volume and the compliance and also shows that they correlate to each other. FIG. 3 shows comparison results between the FCR method described above according to the present invention and the Endo-PAT method of related art. As for the independence of the influential factors, an associated experiment has been conducted in Example 5, which will be described later, and the degree of coincidence between the two methods is examined in Example 6, which will be described later.

Next, a method for estimating the average of SBP values from the pulse wave containing several beats in a finger clamping trial is as follows: In the process in which the pressure applied by each of the cuffs 21 increases, NPV decreases from the point of time when NPVmax is detected as shown in FIG. 2. In the segment before NPVt/NPVmax<0.1 is satisfied, NPVt/NPVmax obtained from pulsation corresponding to several beats is substituted into Expression (2) described above to calculate SBPt for the several beats from the SBPt/FCt for the beats. The average of the SBPt values is determined and the average is used as an estimated value of SBP in the measurement trial.

As described above, since an estimated value of PP can be calculated from an estimated value of SBP and an estimated value of MBP by using Expression (3) described above, one estimated PP value can be obtained per sequence. Assuming that the estimated PP value is constant during one sequence, substituting the estimated PP value into Expression (5) described above eventually allows an FCR ratio for each heartbeat to be obtained from the NPV value and the estimated PP value for each heartbeat for the entire pulsation during the finger cramping trial.

The storage means 4 and the computation processing means 5 described above are formed of a computer, such as a personal computer. The finger arterial dilatability testing program 1a is configured to allow the computer to function as each of the constituent sections described above.

Action of the finger arterial dilatability testing device 1 operated by the finger arterial dilatability testing program 1a according to the present embodiment and the finger arterial dilatability testing method will next be described with reference to FIG. 4.

When the finger arterial dilatability testing device 1 according to the present embodiment is used to measure the FCR ratio, the photoelectric sensor 31 and the cuff 21 are attached in advance to the index finger of each hand of a subject. In the present embodiment, since the cuff 21 is integrated with the light receiver 31b and the integrated structure is wound around the finger, it is therefore unnecessary to provide cuffs 21 having different diameters, but one type of cuff 21 allows optimum attachment in accordance with the finger diameter of each of subjects. Further, the light emitter 31a and the light receiver 31b are allowed to come into intimate contact with the finger, whereby the amount of shift of the optical path in the time course of finger clamping can be minimized.

Thereafter, at the time of rest, the finger cramp means 2 is used to cramp the finger arteries in both hands in accordance with the sequence described above, and the pulse wave detection means 3 is used to measure pulse wave data (step S1), as shown in FIG. 5. After one forearm is occluded at the systolic blood pressure plus a pressure of 50 mmHg for 5 minutes (step S2), at the time of reperfusion, the finger clamp means 2 is used to clamp the finger arteries in both hands in accordance with the sequence described above, and the pulse wave detection means 3 is used to measure pulse wave data (step S3). The pulse wave data for both hands at the time of rest and the data at the time of reperfusion are thus stored in the pulse wave data storage section 42. Further, the cuff pressure data for both hands at the time of rest and the data at the time of reperfusion are stored in the cuff pressure data storage section 43.

In the period during which the finger clamp means 2 cramps each of the fingers, the light emitter 31a in the photoelectric sensor 31 emits light, and the light receiver 31b in the photoelectric sensor 31 detects the amount of light having passed through the tissue and blood vessels in the finger. Hemoglobin in the blood has an absorption spectrum in accordance with which hemoglobin strongly absorbs light having a certain wavelength band. The amount of light having the wavelength band and passing through a living body irradiated with the light therefore changes in accordance with the amount of hemoglobin, which changes as the vascular volume changes. The pulse wave amplifier 32 then amplifies the amount of transmitted light detected by the light receiver 31b, and the pulse wave can thus be detected.

The NPV calculation section 52 then acquires the pulse wave data from the pulse wave data storage section 42 and divides the amplitude of the AC component of the pulse wave data by the average of the DC component thereof to calculate NPV (step S4). The NPV values for both hands at the time of rest and at the time of reperfusion are thus calculated for each heartbeat.

Subsequently, when the FCR method according to the present embodiment is performed by using the original method (step 5: original method), a continuous hemomanometer is attached to each hand of the subject, and the pulse pressure in the finger arteries in each hand is actually measured (step S6). Very accurate pulse pressure for both hands can thus be acquired, whereby an FCR ratio having a small amount of error is calculated.

On the other hand, when the FCR method according to the present embodiment is performed by using the simplified method (step 5: simplified method), the SBP estimation section 54 first acquires the cuff pressure (FCt) at points of time t after NPV is maximized from the cuff pressure data storage section 43. The systolic blood pressure values (SBPt) at the points of time t after NPV is maximized are then calculated by using Expression (2) described above, and the systolic blood pressure values are averaged to derive an estimated systolic blood pressure (SBP) (step S7).

Since the right and left systolic blood pressure values are thus simultaneously estimated, calculating the ratio between the systolic blood pressure values for both hands is likely to result in removal of an error bias associated with the estimation, such as overvaluation or undervaluation. Further, since averaged SBP at a point of time closer to the time when NPV is maximized (time when mean blood pressure is determined) is calculated than in an oscillometric method of related art, the degree of influence of a change in blood pressure is reduced, whereby estimation accuracy is improved.

Subsequently, the pulse pressure estimated value calculation section 55 acquires, as the mean blood pressure (MBP), the cuff pressure at the time when NPV is maximized from the cuff pressure data storage section 43, acquires the systolic blood pressure (SBP) estimated by the SBP estimation section 54, and calculates a pulse pressure estimated value by using Expression (3) described above (step S8). The pulse pressure is thus estimated only from the pulse wave and the cuff pressure without actual measurement of the pulse pressure by using a large, expensive continuous hemomanometer. Further, as described above, since SBP influenced by a change in blood pressure only by a small amount is used, the pulse pressure is estimated with improved accuracy.

The pulse pressure data acquisition section 53 then acquires pulse pressure necessary for calculation of the FCR ratio (step S9). In the present embodiment, in the case of the original method, the pulse pressure data acquisition section 53 acquires an actually measured pulse pressure value as the pulse pressure from a continuous hemomanometer. On the other hand, in the case of the simplified method, the pulse pressure data acquisition section 53 acquires a pulse pressure estimated value calculated by the pulse pressure estimated value calculation section 55 as the pulse pressure.

Finally, the FCR ratio calculation section 56 calculates the index representing the vasodilation response from the finger arteries (FCR ratio) by using Expression (1) described above based on the normalized pulse volume (NPV) calculated by the NPV calculation section 52 and the pulse pressure (PP) acquired by the pulse pressure data acquisition section 53 (step S10). As a result, in the case of the original method, the FCR ratio, which represents the vasodilation response from the finger arteries, is accurately calculated for each heartbeat. On the other hand, in the case of the simplified method, the FCR ratio is calculated for each heartbeat based only on the pulse wave and the cuff pressure without actual measurement of the pulse pressure.

According to the present invention described above, the following advantageous effects are provided:

1. Early signs of arteriosclerosis in the small vessels of the finger arteries can be tested.

2. The following three different structural, functional factors: the vascular endothelial function; the structural stiffness of the arteries; and the functional stiffness influenced by the blood pressure, can be comprehensively evaluated.

3. The FMD method of related art only allows evaluation of the initial response after reperfusion, and the Endo-PAT method of related art only allows evaluation of the delayed response after reperfusion, whereas the present invention allows both the initial response and the delayed response to be assessed in a single test.

4. In the FMD method, an expensive ultrasonic diagnosis device is required and image analysis requires skill and is accompanied by inevitable subjectivity of a tester, whereas according to the present invention, only the pulse wave is measured as a response from a living body, resulting in excellent objectivity, a compact, lightweight, safe, inexpensive, readily operated device.

5. A cuff section required in the Endo-PAT method is a disposable per test, whereas according to the present invention, the cuff 21 can be repeatedly used, and the same cuff 21 allows optimal attachment to a plurality of different subjects, whereby the running cost can be reduced.

6. The FCR ratio provided in the simplified method allows evaluation of the arterial dilatability in a reactive hyperemia state with the aid of the compliance of the finger arteries, whereby an increase in the amplitude of pulsation with no influence of the pulse pressure at the time of reactive hyperemia can be assessed.

7. Although the dynamic compliance in the finger arteries at the time of reactive hyperemia depends on effective pressure acting on blood vessels (transmural pressure), the transmural pressure at the time of measurement of the compliance can be regulated by also using the finger clamp method in accordance with which the cuff 21 clamps a finger, the compliance can be evaluated in consideration of the transmural pressure.

8. Under the circumstances in which arterioles and small arteries differ from each other in terms of endothelial function, the FCR ratio can be calculated for each of a high transmural pressure region and a low transmural pressure region where the arterioles and the small arteries contribute by different amounts, whereby a finger small arterial component and a finger arteriole component represented by the respective FCR ratios can be separately evaluated. According to a medical theory stating that a vascular pathologic change first starts from arterioles and then proceeds to larger arteries, the ability to separately assess the endothelial functions of small arteries and arterioles having different vascular diameters is useful not only in a pathophysiological sense but also in a clinical medicine sense.

Specific examples of the finger arterial dilatability testing program 1a, the finger arterial dilatability testing device 1, and the finger arterial dilatability testing method according to the present invention will next be described.

EXAMPLE 1

In Example 1, whether Expression (2) described above is valid, that is, whether the ratio between SBP and the cuff pressure (SBPt/FCt) can be determined from the ratio of the amplitude of the pulse wave of a certain beat to the maximum amplitude of the pulse wave (NPVt/NPVmax) has been experimentally confirmed.

Specifically, the FCR method was performed on the second finger of each hand of 12 healthy youth subjects, and two continuous hemomanometers (model MUB manufactured by Medisens, INC.) along with the volume compensation method were used to measure the blood pressure for each heartbeat at the third finger of each hand.

For heartbeats under a condition that the cuff pressure was higher than or equal to MBP and NPVt/NPVmax>0.1 was satisfied, the correlation between NPVt/NPVmax and SBPt/FCt was examined. As a result of calculation of the correlation for each of the hands of each of the subjects over the resultant entire segment, the average correlation coefficient and one standard deviation segment (each calculated after Fisher transform and then caused to undergo Fisher inverse transform) were −0.937 (from −0.904 to −0.959) for the left hand and −0.939 (from −0.903 to −0.961) for the right hand.

The value of NPVt/NPVmax that provides SBPt=FCt was 0.372±0.229 (average±SD), which shows that there were differences among individuals. In spite of the fact described above, the regression slope and the intercept for the left hand and those for the right hand of a single person were expected to highly agree with each other. The degree of agreement expressed in a correlation coefficient (r) was r=0.530 and r=0.710, respectively. The value of NPVt/NPVmax that provides SBPt=FCt for the left hand and the value for the right hand of a single person were found to be highly correlated with each other (r=0.819).

According to Example 1 described above, the value of NPVt/NPVmax that provides SBPt=FCt, in other words, the value of NPVt/NPVmax that allows estimation of SBPt from FCt for the left hand and the value for the right hand were found to agree with each other for each individual although there were differences among individuals. Expression (2) described above was thus found to be valid.

EXAMPLE 2

The method described above for estimating SBP and PP from the pulse wave is based on the assumption that the blood pressure during a measurement trial remains unchanged. An error of the eventually calculated FCR ratio is affected how much the assumption is actually correct. In Example 2, the FCR ratio obtained by the simplified method was experimentally compared with the FCR ratio obtained by the original method, and the resultant error was evaluated.

Specifically, a continuous hemomanometer (model MUB manufactured by Medisens, INC.) along with the volume compensation method was used to measure the blood pressure for each heartbeat simultaneously at the third fingers of the hands of 12 healthy youth subjects, and the FCR ratio (FCRo) was calculated from each actually measured value of the pulse pressure for the heartbeat (FCR original method). The degree of agreement of the FCRo with the FCR ratio obtained by the simplified method performed on the second fingers of both hands (FCRs) was evaluated.

(1) Finger Plethysmogram (FPG) Measurement Method

The finger plethysmogram (FPG) was measured by using a device for measuring NPV (model MPN1001 manufactured by Medisens, INC.). The device employs a near-infrared light emitting diode (wavelength: 810 nm) and a photodiode, which were attached to the rear side and the ball side of a base joint part of the second finger of each of the left and right upper arms, respectively, with the finger sandwiched between the light emitting diode and the photodiode. The output from the photodiode was amplified by typical AC (time constant: 0.3 seconds) and DC amplifiers, AD-converted, and then inputted to a personal computer for analysis. The ratio between the pulsation amplitude of the AC component and the average of the DC component of the cardiac cycle is NPV, as described above.

(2) Finger Cramp Method

The cuff 21 for cramping a finger was used to collapse the veins and to control the transmural pressure over a wide range. The cuff 21, which had a width of 4 cm, was so wound that it covered the FPG light source and the sensor from above. At each measurement, the cuff pressure was increased at a constant speed of about 6 mmHg/sec for 25 seconds. During the cuff pressure increasing period, the pulsation amplitude of the pulse wave gradually increases, and when the cuff pressure is equal to the mean blood pressure, no load acts on the arteries and the vascular compliance is maximized, resulting in maximum NPV. In other words, the finger mean blood pressure (MBPs) is equal to the cuff pressure at the time when NPV is maximized.

After the cuff pressure becomes equal to the mean blood pressure, continuously increasing the cuff pressure results in a decrease in the amplitude of the pulse wave. In consideration of this phenomenon, the amount of air flowing into the cuff 21 was so adjusted that the pressure acting on the finger was removed when the amplitude of the pulse wave decreased to about 10% of its maximum value. The 25-second cramping phase, which was called a measurement trial, was repeated with a 5-second non-cramping phase interposed between the cramping phases.

The MBPs and the systolic blood pressure estimated value (SBPs), the latter of which was calculated with reference to a fixed value, in each measurement trial were only measured once when NPV was maximized and for pulsation corresponding to several beats where NPV turned to decrease. The difference between SBPs and the diastolic blood pressure (minimum blood pressure), the latter of which was determined by an approximation equation, was defined as the pulse pressure estimated value (PPs).

(3) Measurement at the Time of Rest

During the repeated finger clamping trial described above, MBPs and PPs as well as a compliance index for each measurement trial (CIs=NPV/PPs) were determined. The measurement described above was performed on the pulse wave in each hand.

(4) Measurement at the Time of Reperfusion (Reactive Hyperemia) After 5-minute Occlusion For 3 minutes after the occlusion was released, during the finger clamping trial described above repeated every 30 seconds, MBPs and PPs as well as the compliance index (CIs=NPV/PPs) for each measurement trial were determined. The measurement described above was performed on the pulse wave in each hand.

(5) Calculation of FCR Ratio by Using Simplified Method

The FCR ratio based on the simplified method (FCRs) was calculated by using Expression (5) described above every 30 seconds after the reperfusion.

(6) Calculation of FCR Ratio by Using Original Method

As a reference to be compared with the simplified method described above, the original method according to which the pulse pressure was actually measured for each heartbeat was performed. That is, in the simplified method, the same PPs was used during one measurement trial, whereas in the original method, an actually measured value (PPo) actually measured for each heartbeat from a continuous blood pressure waveform was used to calculate CIo for a single heartbeat (CIo=NPV/PPo). As in the simplified method, the FCR ratio based on the original method (FCRo) was calculated by using Expression (1) described above every 30 seconds after the reperfusion.

(7) In the arterial system, the pressure gradient produced when blood flows from the central main arteries into the peripheral arterioles causes the internal pressure in an artery having a smaller vascular diameter to decrease by a greater amount. The largest, steepest pressure decrease occurs in the arterioles. From the viewpoint of finger clamping, in the process of gradual increase in the cuff pressure, the blood vessels are collapsed sequentially from a smaller one to a larger one. The transmural pressure (Pt) acting on the arterial wall is calculated by the following equation: effective pressure=MBPs−cuff pressure (FC).

When CI is calculated only for the region where FC is still low, that is, the high transmural pressure region defined by "Pt>MBPs/2" (in other words, "FC<MBPs/2"), the compliance for the component of the transmural pressure characterized in that arterioles contribute by a greater amount can be evaluated. Further, when CI is calculated only for the region where FC is high, that is, the low transmural pressure region defined by "Pt<MBPs/2" (in other words, "FC>MBPs/2"), the component of the transmural pressure in the small arteries, which are relatively thick among the finger arteries, can be evaluated (method for separating low transmural pressure component and high transmural pressure component from each other in FIG. 2).

In Example 2, to evaluate the FCR ratio in the form of the high and low transmural pressure components separate from each other, each of FCRs and FCRo described above was expressed as collective values of averages in the two transmural pressure regions described above. Specifically, for 5 minutes after reperfusion performed on the 12 subjects, 10 measurement trials every 30 seconds were made, and the degree of agreement between FCRs and FCRo was drawn in a scatter diagram. As shown in FIG. 6, r=0.823 for the high transmural pressure component, and as shown in FIG. 7, r=0.772 for the low transmural pressure component.

According to Example 2 described above, in spite of a variety of error factors, the FCR ratio based on the original method and the FCR ratio based on the simplified method were clearly found to highly agree with each other.

EXAMPLE 3

In Example 3, the simplified method was performed, and the FMD method, which is a medically standard method used in an endothelial function test, was performed at the same time to experimentally evaluate the degree of agreement between the two methods.

Specifically, for 45 healthy youth subjects, % FMD based on the FMD method and the FCR ratio based on the simplified method were compared with each other. It was assumed that the measurement method was made by using the same method as in Example 2 described above. In addition, a dedicated measurement device (model UNEXEF manufactured by UNEX CORPORATION) was used to measure % FMD based on the FMD method simultaneously with the simplified method. The measurement of % FMD was made in accordance with a standard procedure by a skilled clinical laboratory technician.

The FCR ratio based on the simplified method is the ratio between compliance values on the right and left sides (occluded side/control side) and is normalized by the ratio at the time of rest. For an analysis segment over which the finger cuff pressure is greater than or equal to 50% of the mean blood pressure but smaller than or equal to the mean blood pressure (arterioles were blocked and a component that involves only thick finger blood vessels was extracted), the FCR ratio was defined to be the average of those in the following two finger cramping trials: a period for 25 seconds immediately after occlusion was eliminated; and a period from 30 to 55 seconds after the occlusion was eliminated (initial response in FIG. 5).

As a result of the experiment, single correlation between % FMD based on the FMD method and the FCR ratio based on the simplified method was significant (r=0.474, p<0.01), and partial correlation based on the following covariates remained significant (r=0.454, p<0.01): the gender; the age; the diameter of the forearm arteries, the cardio ankle vascular index (CAVI) on the right side of the hyperemia side; mean blood pressure in a finger of the right hand at the time of rest before occlusion; and the compliance initial value for the finger of the right hand at the time of rest before occlusion, which were all examined in advance.

As a result of subsequent stepwise multiple regression analysis using the FCR ratio based on the simplified method as a target variable, a model according to which the FCR ratio based on the simplified method is described based on the following two variables was significant: % FMD based on the FMD method (standard partial regression coefficient $\beta$=0.446, p<0.01); and the finger arterial elasticity index FEI (standard partial regression coefficient $\beta$=0.292, p<0.05), which has been uniquely developed by the inventor of the present application, and a multiple correlation coefficient R of the model was 0.567 (p<0.001), as shown in FIG. 8.

These results agree with initial expectation of "the FCR ratio reflects the vascular endothelial function and is also influenced by the stiffness of the finger arteries, and the FCR ratio increases as the finger arteries are softened." It is, however, found that % FMD based on the FMD method and the FCR ratio based on the simplified method agree with each other only by a small amount. It is believed that a primary cause for this is the fact that the endothelial function differs between a site in the brachial artery, which is large artery, and a site in the small arterioles, and that the small degree of agreement described above does deny the validity of the simplified method.

On the other hand, as described above, the Endo-PAT method, which evaluates an increase in the pulsation amplitude at the time of reactive hyperemia by using finger plethysmogram, has been increasingly used in clinical applications. According to a worldwide research trend relating to the vascular endothelial function testing, however, large-scale studies in which the Endo-PAT method is compared with the FMD method applied to forearm arteries have been conducted, and it is widely accepted that the two methods poorly correlate with each other, reflect different physiological functions, and have respective independent pathophysiological significances.

Example 3 therefore suggests that the degree of agreement between % FMD based on the FMD method and the FCR ratio based on the simplified method is greater than the degree of agreement between % FMD based on the FMD method and the PAT ratio based on the Endo-PAT method. Further, multiple correlation between % FMD and the FCR ratio has been proved significant in multiple regression estimate using the initial response in the simplified method as a dependent variable and % FMD and the finger arterial elasticity index (FEI) as explanatory variables. That is, both the functional stiffness depending on the blood pressure and the structural stiffness of the finger arterioles (FSI) contribute to FEI, and each of the vascular endothelial function, the blood pressure, and the vascular structural stiffness has been accepted as an independent marker for vascular health. It can therefore be said that the initial response of the FCR ratio based on the simplified method provides a totally new vascular health marker as compared with methods of related art in a sense that the initial response comprehensively reflects both the vascular endothelial function and the functional stiffness and structural stiffness of the arterioles.

EXAMPLE 4

In Example 4, a prototype multi-use testing device was fabricated. The prototype multi-use testing device was capable of testing not only the FCR ratio but also the finger arterial elasticity index (FEI) and a finger arterial stiffness index (FSI) derived from FEI. FIG. 9 shows the exterior appearance of the multi-use testing device, and FIG. 10 shows a waveform monitor screen during measurement using bundled software containing the finger arterial dilatability testing program 1a.

The main body of the multi-use testing device has a size roughly corresponding to three small-sized paperbacks stacked on each other and is hence compact and lightweight. The main body receives power from a PC via USB connection, and a signal from the main body is outputted via USB connection to the PC. An LED is so fixed to a finger that a mounting portion of the LED is attached to the nail on the rear side of the finger with a tape. A photosensor is so attached that it is in intimate contact with the ball side of the finger, and the cuff 21 integrated with the sensor is wound around the finger and fixed by using a surface fastener. Employing the attachment method described above eliminates the need for providing a plurality of cuffs 21 having different diameters, but one type of cuff 21 allows optimum attachment in accordance with the finger diameter of each subject. Further, the LED and the photosensor are allowed to come into intimate contact with the finger, whereby the amount of shift of the optical path in the time course of the finger cramping can be minimized.

The bundled software can automatically control the sequence of finger cramping, display the pulse wave inputted to the personal computer and determine NPV and the cuff pressure for each heartbeat, and save a result along with the waveform for the beat in the form of a csv file. Further, after an artifact is removed based on offline visual inspection, NPV and the cuff pressure can be recalculated.

FIG. 10 shows a waveform in a case where the measurement is made simultaneously on fingers of the right and left hands at the time of rest. In FIG. 10, the line extending gradually upward with time represents the cuff pressure, the waveform having a large amplitude represents the AC component of the pulse wave, and the waveform having a small amplitude represents the DC component of the pulse wave. Each vertical line shows identification (systolic period and diastolic period) for each beat. In Example 4, since the A-side hand is positioned at a higher level than the B-side hand with respect to the position of the heart, the blood pressure on the side A is lower than that on the side B.

Example 4 described above shows that the prototype multi-purpose testing device, which is compact, lightweight, simple, safe, and inexpensive and can be readily operated by a clinical laboratory technician and a physician, can be introduced into domestic and overseas joint research facilities including medical facilities for large-scale accumulation of clinical data. Further, the device, which simultaneously measures the mean blood pressure and the stiffness, can evaluate relative proportions at which they contribute to the FCR ratio.

EXAMPLE 5

In Example 5, as an approach for distinguishing whether a subject is a healthy person or a diabetes patient, an experiment was conducted to find which is superior, the FCR method or the Endo-PAT method.

Specifically, each of subjects including 24 healthy youth females and 37 diabetes patients underwent measurement of the FCR ratio according to the present invention and the PAT ratio according to the Endo-PAT method. FIG. 11(a) shows results of the measurement. At the same time, the amounts of change in the pulse pressure and the mean blood pressure were measured for each of the subjects. FIG. 11(b) shows results of the measurement. The average of the compliance at the time of reperfusion and the compliance before occlusion was used as the FCR ratio, and the average of NPV at the time of reperfusion and NPV before occlusion was used as the PAT ratio.

FIG. 11(a) shows that the difference in the FCR ratio between the healthy youth females and the diabetes patients is greater than the difference in the PAT ratio between the two types of subject. The reason for this is that the width of a change in each of the pulse pressure and the mean blood pressure in the healthy youth females is greater than the width of the change in the diabetes patients, as shown in FIG. 11(b). That is, at the time of reperfusion, the FCR ratio increases because the vascular endothelial function works, whereas the PAT ratio does not increase as greatly as the FCR ratio because the pulse pressure decreases. The Endo-PAT method, which uses the pulsation volume, therefore undesirably underestimates the influence of the endothelial function. Since the amount of decrease in the pulse pressure in the healthy youth females is greater than the amount in the diabetes patients as shown in FIG. 11(b), the degree of the influence of the underestimation described above in the healthy females is greater than the degree of influence in the diabetes patients.

Example 5 described above shows that the FCR method is superior to the Endo-PAT method as an approach for clearly distinguishing whether a subject is a healthy person or a diabetes patient.

EXAMPLE 6

In Example 6, the superiority of the FCR method to the Endo-PAT method was experimentally confirmed by examining the degree of agreement between the FCR ratio according to the present invention and the PAT ratio according to the Endo-PAT method.

Specifically, each of 35 diabetes patients underwent measurement of the FCR ratio and the PAT ratio, and a partial correlation coefficient that correlates the two types of ratio with each other was calculated. In addition to the partial correlation coefficient calculation, a similar partial correlation coefficient is calculated by using a PAT ratio obtained by statistically removing all the following elements: the pulse pressure; the mean blood pressure; and the stiffness, which are influential factors that influence the PAT ratio. FIG. 12 shows results of the calculation. In Example 6, since the FCR ratio depends on the magnitude (previous value) of the compliance before occlusion and at the time of rest, partial correlation in which the previous value is controlled is shown. Further, in Example 6, the PAT ratio is a value having undergone correction of the influence of the pulsation volume at the time of rest.

As shown in FIG. 12, when the influences of the influential factors on the PAT ratio are not removed, the partial correlation coefficient that correlates the FCR ratio and the PAT ratio with each other is about 0.5, which means that the two ratios poorly correlate with each other. The reason for this is that the Endo-PAT method is influenced by the pulse pressure and the mean blood pressure and is hence theoretically incorrect in one aspect. On the other hand, when the influences of the influential factors on the PAT ratio are removed, the partial correlation coefficient that correlates the FCR ratio and the PAT ratio with each other is about 0.7, showing an improvement in the degree of agreement between the two ratios.

Example 6 described above shows that the Endo-PAT method, when its theoretical disadvantages are corrected, approaches the FCR method according to the present invention in terms of usability.

EXAMPLE 7

In Example 7, whether a subject belongs to a healthy group or a diabetes group was experimentally determined by using both the finger arterial elasticity index (FEI) according to Japanese Patent No. 5,039,123 described above and the FCR ratio according to the present invention. The finger arterial elasticity index (FEI) is expressed as a linear regression gradient (n) of the following Expression (4):

$$ln(NPV) = ln(bn) - n \cdot Pr \qquad \text{Expression (4)}$$

where b: constant, and

Pr: relative cuff pressure (difference between the cuff pressure at the time when the amplitude of the pulse wave is maximized and each cuff pressure).

Specifically, each of subjects including 31 healthy youth females and 37 diabetes patients (males and females) underwent measurement of the FCR ratio according to the present invention and the finger arterial elasticity index (FEI). FIG. 13($a$) shows a result of the measurement.

A multi-regression equation using a numerical target variable showing whether a subject belongs to a healthy group or a diabetes group was calculated as a discrimination function based on a group of data having two variables, FEI and the FCR ratio (discrimination function calculation step). FIG. 13($a$) shows the discrimination function. Subsequently, FEI and the FCR ratio of a subject under discrimination were substituted into the discrimination function to calculate a discrimination score (discrimination score calculation step). FIG. 13($b$) shows results of the calculation. Further, whether the subject under discrimination belonged to a healthy group or a diabetes group was determined based on the discrimination score (diabetes discrimination step).

As shown in FIG. 13($b$), when the discrimination scores in the healthy group are compared with those in the diabetes group, the scores in the two groups clearly separate from each other over the positive and negative regions and hence very poorly overlap with each other. It can therefore be said that the calculated discrimination function accurately determines whether a subject belongs to the healthy group or the diabetes group. Further, as shown in FIG. 13($c$), the discrimination score based on both FEI and the FCR ratio is useful also in clinical diagnosis because the discrimination score does not correlate with the mean blood pressure in a finger or hence does not depend on the blood pressure.

Example 7 described above shows that using both the finger arterial elasticity index (FEI) according to Japanese Patent No. 5,039,123 and the FCR ratio according to the present invention allows accurate discrimination of whether a subject belongs to the healthy group or the diabetes group and hence an improvement in usefulness in clinical diagnosis.

EXAMPLE 8

In Example 8, the diabetes discrimination function according to Example 7 described above was implemented in the finger arterial dilatability testing device 1 and the finger arterial dilatability testing program 1$a$ according to the present invention.

Specifically, the finger arterial dilatability testing program 1$a$ was so implemented in the finger arterial dilatability testing device 1, which works as a computer, that the storage means 4 functions as an FEI storage section that stores FEI of each subject, and the computation processing means 5 functions as a discrimination function calculation section that executes the discrimination function calculation step described in Example 7, a discrimination score calculation section that executes the discrimination score calculation step described in Example 7, and a diabetes discrimination section that executes the diabetes discrimination step described in Example 7.

In the above description, the discrimination function calculation section calculates the multi-regression equation using the numerical target variable showing whether a subject belongs to the healthy group or the diabetes group as the discrimination function based on a group of data having the following two variables: FEI stored in the FEI storage section; and the FCR ratio calculated by the FCR ratio calculation section 56. Further, the discrimination score calculation section calculates the discrimination score by substituting FEI and the FCR ratio of a subject under discrimination into the discrimination function calculated by the discrimination function calculation section. The diabetes discrimination section determines whether the subject under discrimination belongs to the healthy group or the diabetes group based on the discrimination score calculated by the discrimination score calculation section.

In the configuration described above, when the group of data having the following two variables: FEIs and the FCR ratios associated with a predetermined number of subjects were given, the discrimination function calculation section calculated the discrimination function. Subsequently, when FEI and the FCR ratio of a subject under discrimination were given, the discrimination score calculation section substituted the values into the discrimination function to calculate the discrimination score. The diabetes discrimination section then determined whether the subject under discrimination belonged to the healthy group or the diabetes group based on the discrimination score.

Example 8 described above shows that the diabetes discrimination function can be added to and implemented in the finger arterial dilatability testing device 1 and the finger arterial dilatability testing program 1$a$ according to the present invention.

In Example 8, the FEI storage section, which stores FEI measured by the finger arterial elasticity measurement device according to Japanese Patent No. 5,039,123, was provided, but the configuration described above is not necessarily employed. That is, a function of calculating FEI may be separately implemented in the finger arterial dilatability testing device 1 and the finger arterial dilatability testing program 1$a$ according to the present invention.

EXAMPLE 9

In Example 9, whether or not a subject was a diabetes patient was experimentally determined in a case where only the FCR ratio according to the present invention was used, a case where FEI was used as well as the FCR ratio, and a case where the finger mean blood pressure was used as well as the FCR ratio and FEI.

Specifically, each of subjects including 39 healthy females and 49 diabetes patients underwent measurement of the FCR ratio, FEI, and the finger mean blood pressure. A discrimination function in the case where only the FCR ratio was used, a discrimination function in the case where both the FCR ratio and FEI were used, and a discrimination function in the case where the FCR ratio, FEI, and all the finger mean blood pressure were used were calculated. The FCR ratio, FEI, and the finger mean blood pressure of each of the subjects were substituted into the calculated discrimination functions to determine the discrimination scores, and whether the subject was a diabetes patient was determined. FIG. 14 shows results of the experiment.

As shown in FIG. 14($a$), in the case where only the FCR ratio was used, a predictive value representing the proportion at which a healthy females was correctly predicted as a healthy female and a diabetes patient was correctly predicted as a diabetes patient was 76.1%. On the other hand, as shown in FIG. 14($b$), in the case where FEI was used as well as the FCR ratio, the predictive value was improved to 86.4%. Further, as shown in FIG. 14($c$), in the case where the finger mean blood pressure was used as well as the FCR ratio and FEI, the predictive value was improved to 95.5%.

Example 9 described above shows that the predictive value representing discrimination of a healthy female and a diabetes patient from each other is higher in the case where FEI was used as well as the FCR ratio than the case where only the FCR ratio was used, and the predictive value is the highest in the case where the finger mean blood pressure was used as well as the FCR ratio and FEI.

The finger arterial dilatability testing method, the finger arterial dilatability testing device 1, and the finger arterial dilatability testing program 1a according to the present invention are not limited to those in the embodiment and Examples described above and can be changed as appropriate.

For example, a display table showing the vasodilation response of the finger arteries (soft, normal, and hard, for example) in correspondence with numerical ranges of the FCR ratio may be stored in the storage means 4, and data representing the vasodilation response of the finger arteries may be outputted from display means and print means that are not shown based on the value of the FCR ratio calculated by the FCR ratio calculation section 56.

Further, in the present embodiment described above, the FCR ratio is calculated by normalizing the ratio of the compliance index at the time of reperfusion between the right and left hands by the ratio of the compliance index at the time of rest between the right and left hands. It is, however, believed that the ratio of the compliance index between different fingers of one of the hands instead of the ratio of the compliance index between both hands may be used. That is, the compliance index of a finger having undergone occlusion and the compliance index of a finger having undergone no occlusion may be used as CIr and CIc in Expression (1) described above.

INDUSTRIAL APPLICABILITY

In recent years, prevention of lifestyle related diseases has been the most important issue in the national health care policy, and in view of a steep increase in the number of lifestyle related diseases, specific medical checkup and health guidance directed to metabolic syndromes have started since 2008. Among them, diagnosis and intervention relating to vascular endothelial function disorders including arteriosclerosis are particularly important in prevention of cardiovascular diseases and cerebrovascular diseases. For example, diabetes, which is one of the lifestyle related diseases, causes a variety of complications. Those who lost their eyesight due to diabetic retinopathy amount to about 3,000 persons on an annual basis. Ripple effects resulting from diabetes are as follows:

First, clinical cases in which an arterial endothelial function testing based on the FCR method is directly useful includes diabetic retinopathy, which is accompanied by microangiopathy and becomes a primary cause of loss of one's sight, occlusion of retinal vein, age-related macular degeneration, heart failure in the circulatory organ region, diabetic nephropathy, which leads to kidney dialysis treatment, hypertension, which accelerates arteriolosclerosis, and erectile dysfunction, behind which arteriosclerosis acts.

Second, a pathological state of small arteries, which appears in the earliest stage in the natural history of arteriosclerosis antecedent to arteriosclerosis and hypertrophy of large arteries, is believed to be an important index in preventive medicine. That is, the arterial elasticity and stiffness test (FEI/FSI method), on which the research group to which the inventor of the present application belongs has been playing a leading role, and the arterial endothelial function testing (FCR method) according to the present invention are useful for disease prediction, screening, diagnosis, and long-term medical observation in a pre-clinical stage of the entire lifestyle related diseases including ischemic heart diseases (angina and myocardial infarction), cerebral infarction, and other serious diseases and provide a wider range of ripple effects in medical sites.

Third, since an early decrease in vascular health is reversible, the present invention is expected to be used as a biomarker, for example, in health management of the general healthy population, evaluation of chronically accumulated daily stress, and judgment of a health guidance intervention effect. For example, in an intervening specific health guidance for metabolic syndromes, diabetes, and other diseases, a useful biomarker is required as an intervention evaluation index.

Therefore, future applications of the FCR method and future fields where the FCR method is used may include a very wide range of health promotion and health assistance sites, that is, school infirmary where children and students are taken care of, health management facilities for professional workers, commercial sport facilities, health education and health management in facilities providing long-term care to the elderly and other places, and evaluation of health food and medicine.

If it is possible to further reduce the size of the device and simplify the device, it is conceivable that a hemomanometer having the device incorporated therein is widely spread as an inexpensive health management device for household use. That is, as in the case of the FMD method and the Endo-PAT method, the FCR method is believed to contribute to a wide range of medical life industries, such as medicine, welfare, education, and food health-related industries, which "enhance QOL (Quality Of Life)" of the people in accordance with an increase in not only supply to medical facilities that meets demand in the medical insurance system but also potential demand for disease prevention and care prevention under the background of an aging society in the nation.

REFERENCE SIGNS LIST

1: Finger arterial dilatability testing device
1a: Finger arterial dilatability testing program
2: Finger clamp means
3: Pulse wave detection means
4: Storage means
5: Computation processing means
21: Cuff
22: Air pump
31: Photoelectric sensor
31a: Light emitter
31b: Light receiver
32: Pulse wave amplifier
41: Program storage section
42: Pulse wave data storage section
43: Cuff pressure data storage section
51: Cuff pressure control section
52: NPV calculation section
53: Pulse pressure data acquisition section
54: SBP estimation section
55: Pulse pressure estimated value calculation section
56: FCR ratio calculation section

The invention claimed is:

1. A finger arterial dilatability testing method for testing a vasodilation response of finger arteries, the method comprising:

a pulse wave data storage step of storing pulse wave data, the pulse wave data being measured from:
one of the fingers of a first hand of a patient and one of the fingers of a second hand of the patient while being pressed at a predetermined sequence at the time of rest and at the time of reperfusion after a forearm of one of the first and second hands is caused to undergo occlusion, or
a first one and a second one of fingers of one of the first hand and the second hand of the patient while being pressed at the predetermined sequence at the time of rest and at the time of reperfusion after one of the first and second ones of the fingers is caused to undergo occlusion;
a normalized pulse volume (NPV) calculation step of calculating, based on the pulse wave data stored in the pulse wave data storage step during the time of rest and the time of reperfusion, the NPV, which is obtained by dividing the amplitude of an AC component of a pulse wave by the average of a DC component of the pulse wave after storing the pulse wave data, for each heartbeat;
a pulse pressure (PP) data acquisition step of acquiring the PP after calculating the NPV; and
a finger arterial compliance response ratio (FCR ratio) calculation step of calculating the FCR ratio, which is an index representing a vasodilation response of the finger arteries for each heartbeat, the FCR ratio being one of (1) the ratio between compliance indices for the first and second hands at the time of reperfusion normalized by the ratio between the compliance indices for the first and second hands at the time of rest when the pulse wave data is measured from the one of the fingers of the first hand of a patient and the one of the fingers of the second hand of the patient, the compliance index being an index obtained by dividing the NPV calculated in the NPV calculation step by the PP acquired in the pulse pressure data acquisition step, and (2) the ratio between the compliance indices for the first and second ones of the fingers of the one of the first hand and the second hand at the time of reperfusion normalized by the ratio between the compliance indices for the first and second ones of the fingers of the one of the first hand and the second hand at the time of rest when the pulse wave data is measured from the first one and the second one of the fingers of the one of the first hand and the second hand of the patient,
wherein the FCR ratio is expressed by the following Expression (1):

$$\text{FCR ratio} = [ln(CI_r/CI_c)]_y - [ln(CI_r/CI_c)]_x \qquad \text{Expression (1)}$$

where CI: compliance index (=NPV/PP),
r: subscript indicating hand or finger that undergoes occlusion,
c: subscript indicating hand or finger that undergoes no occlusion,
x: subscript indicating the time of rest, and
y: subscript indicating the time of reperfusion, and
the predetermined sequence is an action in which a cuff pressure is increased from zero at a predetermined rate and in which the cuff pressure is released until the cuff pressure returns to zero.

2. The finger arterial dilatability testing method according to claim 1, further comprising:
a cuff pressure data storage step of storing cuff pressure applied by a cuff that presses each finger;
a systolic blood pressure (SBP) estimation step of calculating systolic blood pressure values (SBPt) at points of time t after the NPV is maximized by using the following Expression (2) and averaging the calculated SBPt to derive an estimated SBP:

$$\text{SBP}t = (b \times (\text{NPV}t/\text{NPVmax}) + a) \times \text{FC}t \qquad \text{Expression (2)}$$

where NPVt: NPV at time t,
NPVmax: maximum NPV,
FCt: cuff pressure (FC) at time t, and
a, b: constant; and
a pulse pressure estimated value calculation step of calculating a pulse pressure estimated value (PPs) by using the following Expression (3) based on a mean blood pressure (MBP) and the SBP estimated in the SBP estimation step, the MBP being the cuff pressure that is stored in cuff pressure data storage step and that is at the time when the NPV is maximized:

$$\text{PP}s = (\text{SBP} - \text{MBP}) \times 3/2 \qquad \text{Expression (3), and}$$

in the pulse pressure data acquisition step, the pulse pressure estimated value calculated in the pulse pressure estimated value calculation step is acquired as the pulse pressure.

3. The finger arterial dilatability testing method according to claim 1, further comprising:
a discrimination function calculation step of calculating a discrimination function for determining whether a patient under discrimination belongs to a healthy group or a diabetes group based on group of data having two variables, a finger arterial elasticity index (FEI), which is calculated as a linear regression gradient (n) of the following Expression (4), and the FCR ratio:

$$ln(\text{NPV}) = ln(bn) - n \cdot \text{Pr} \qquad \text{Expression (4)}$$

where b: constant, and
Pr: relative cuff pressure (difference between the cuff pressure at the time when the amplitude of the pulse wave is maximized and each cuff pressure);
a discrimination score calculation step of substituting the FEI and the FCR ratio of the patient under discrimination into the discrimination function to calculate a discrimination score; and
a diabetes discrimination step of determining whether the patient under discrimination belongs to the healthy group or the diabetes group based on the discrimination score.

4. A finger arterial dilatability testing device for testing a vasodilation response of finger arteries, the device comprising:
a pulse wave data storage section that stores pulse wave data, the pulse wave data being measured from:
one of the fingers of a first hand of a patient and one of the fingers of a second hand of the patient while being pressed at a predetermined sequence at the time of rest and at the time of reperfusion after a forearm of one of the first and second hands is caused to undergo occlusion, or
a first one and a second one of fingers of one of the first hand and the second hand of the patient whole being pressed at the predetermined sequence at the time of rest and at the time of reperfusion after one of the first and second ones of the fingers is caused to undergo occlusion;
a normalized pulse volume (NPV) calculation section that calculates, based on the pulse wave data stored in the pulse wave data storage section during the time of rest and the time of reperfusion, the NPV, which is obtained by dividing the amplitude of an AC component of a pulse wave by the average of a DC component of the pulse wave after storing the pulse wave data, for each heartbeat;

a pulse pressure (PP) data acquisition section that acquires the PP after calculating the NPV; and a finger arterial compliance response ratio (FCR ratio) calculation section that calculates the FCR ratio, which is an index representing a vasodilation response of the finger arteries for each heartbeat, the FCR ratio being one of (1) the ratio between compliance indices for the first and second hands at the time of reperfusion normalized by the ratio between the compliance indices for the first and second hands at the time of rest when the pulse wave data is measured from the one of the fingers of the first hand of a patient and the one of the fingers of the second hand of the patient, the compliance index being an index obtained by dividing the NPV calculated by the NPV calculation section by the PP acquired by the pulse pressure data acquisition section, and (2) the ratio between the compliance indices for the first and second ones of the fingers of the one of the first hand and the second hand at the time of reperfusion normalized by the ratio between the compliance indices for the first and second ones of the fingers of the one of the first hand and the second hand at the time of rest when the pulse wave data is measured from the first one and the second one of the fingers of the one of the first hand and the second hand of the patient, wherein the FCR ratio is expressed by the following Expression (1):

$$FCR\ ratio=[ln(CIr/CIc)]y-[ln(CIr/CIc)]x \qquad \text{Expression (1)}$$

where CI: compliance index (=NPV/PP),
r: subscript indicating hand or finger that undergoes occlusion,
c: subscript indicating hand or finger that undergoes no occlusion,
x: subscript indicating the time of rest, and
y: subscript indicating the time of reperfusion, and
the predetermined sequence is an action in which a cuff pressure is increased from zero at a predetermined rate and in which the cuff pressure is released until the cuff pressure returns to zero.

5. The finger arterial dilatability testing device according to claim 4, further comprising:

a cuff pressure data storage section that stores cuff pressure applied by a cuff that presses each finger;

a systolic blood pressure (SBP) estimation section that calculates systolic blood pressure values (SBPt) at points of time t after the NPV is maximized by using the following Expression (2) and averages the calculated SBPt to derive an estimated SBP:

$$SBPt=(b\times(NPVt/NPVmax)+a)\times FCt \qquad \text{Expression (2)}$$

where NPVt: NPV at time t,
NPVmax: maximum NPV,
FCt: cuff pressure (FC) at time t, and
a, b: constant; and a pulse pressure estimated value calculation section that calculates a pulse pressure estimated value (PPs) by using the following Expression (3) based on a mean blood pressure (MBP) and the SBP estimated by the SBP estimation section, the MBP being the cuff pressure that is stored in cuff pressure data storage section and that is at the time when the NPV is maximized:

$$PPs=(SBP-MBP)\times 3/2 \qquad \text{Expression (3), and}$$

the pulse pressure data acquisition section acquires the pulse pressure estimated value calculated by the pulse pressure estimated value calculation section as the pulse pressure.

6. The finger arterial dilatability testing device according to claim 4, further comprising:

a discrimination function calculation section that calculates a discrimination function for determining whether a patient under discrimination belongs to a healthy group or a diabetes group based on group of data having two variables, a finger arterial elasticity index (FEI), which is calculated as a linear regression gradient (n) of the following Expression (4), and the FCR ratio:

$$ln(NPV)=ln(bn)-n\cdot Pr \qquad \text{Expression (4)}$$

where b: constant, and
Pr: relative cuff pressure (difference between the cuff pressure at the time when the amplitude of the pulse wave is maximized and each cuff pressure);

a discrimination score calculation section that substitutes the FEI and the FCR ratio of the patient under discrimination into the discrimination function to calculate a discrimination score; and a diabetes discrimination section that determines whether the patient under discrimination belongs to the healthy group or the diabetes group based on the discrimination score.

7. A non-transitory computer-readable recording medium storing a finger arterial dilatability testing program for testing a vasodilation response of finger arteries, the program causing a computer to function as:

a pulse wave data storage section that stores pulse wave data, the pulse wave data being measured from:
one of the fingers of a first hand of a patient and one of the fingers of a second hand of the patient while being pressed at a predetermined sequence at the time of rest and at the time of reperfusion after a forearm of one of the first and second hands is caused to undergo occlusion, or
a first one and a second one of fingers of one of the first hand and the second hand of the patient while being pressed at the predetermined sequence at the time of rest and at the time of reperfusion after one of the first and second ones of the fingers is caused to undergo occlusion;

a normalized pulse volume (NPV) calculation section that calculates, based on the pulse wave data stored in the pulse wave data storage section during the time of rest and the time of reperfusion, the NPV, which is obtained by dividing the amplitude of an AC component of a pulse wave by the average of a DC component of the pulse wave after storing the pulse wave data, for each heartbeat;

a pulse pressure (PP) data acquisition section that acquires the PP after calculating the NPV; and a finger arterial compliance response ratio (FCR ratio) calculation section that calculates the FCR ratio, which is an index representing a vasodilation response of the finger arteries for each heartbeat, the FCR ratio being one of (1) the ratio between compliance indices for the first and second hands at the time of reperfusion normalized by the ratio between the compliance indices for the first and second hands at the time of rest when the pulse wave data is measured from the one of the fingers of the first hand of a patient and the one of the fingers of the second hand of the patient, the compliance index being an index obtained by dividing the NPV calculated by the NPV calculation section by the PP acquired by the pulse pressure data acquisition section, and (2) the ratio between the compliance indices for the first and second ones of the fingers of the one of the first hand and the second hand at the time of reperfusion normalized by the ratio between the compliance indices for the first and second ones of the fingers of the one of the first hand and the second hand at the time of rest when the pulse wave data is measured from the first one and the second one of the fingers of the one of the first hand and the second hand of the patient, wherein the FCR ratio is expressed by the following Expression (1):

$$FCR\ ratio = [ln(CIr/CIc)]y - [ln(CIr/CIc)]x \qquad \text{Expression (1)}$$

where CI: compliance index (=NPV/PP),
r: subscript indicating hand or finger that undergoes occlusion,
c: subscript indicating hand or finger that undergoes no occlusion,
x: subscript indicating the time of rest, and
y: subscript indicating the time of reperfusion, and
the predetermined sequence is an action in which a cuff pressure is increased from zero at a predetermined rate and in which the cuff pressure is released until the cuff pressure returns to zero.

8. The non-transitory computer-readable recording medium storing the finger arterial dilatability testing program according to claim 7, the program causing the computer to further function as:
a cuff pressure data storage section that stores cuff pressure applied by a cuff that presses each finger;
a systolic blood pressure (SBP) estimation section that calculates systolic blood pressure values (SBPt) at points of time t after the NPV is maximized by using the following Expression (2) and averages the calculated SBPt to derive an estimated SBP:

$$SBPt = (b \times (NPVt/NPVmax) + a) \times FCt \qquad \text{Expression (2)}$$

where NPVt: NPV at time t,
NPVmax: maximum NPV,
FCt: cuff pressure (FC) at time t, and
a, b: constant; and
a pulse pressure estimated value calculation section that calculates a pulse pressure estimated value (PPs) by using the following Expression (3) based on a mean blood pressure (MBP) and the SBP estimated by the SBP estimation section, the MBP being the cuff pressure that is stored in cuff pressure data storage section and that is at the time when the NPV is maximized:

$$PPs = (SBP - MBP) \times 3/2 \qquad \text{Expression (3), and}$$

the pulse pressure data acquisition section acquires the pulse pressure estimated value calculated by the pulse pressure estimated value calculation section as the pulse pressure.

9. The non-transitory computer-readable recording medium storing the finger arterial dilatability testing program according to claim 7, the program causing the computer to further function as:
a discrimination function calculation section that calculates a discrimination function for determining whether a patient under discrimination belongs to a healthy group or a diabetes group based on group of data having two variables, a finger arterial elasticity index (FEI), which is calculated as a linear regression gradient (n) of the following Expression (4), and the FCR ratio:

$$ln(NPV) = ln(bn) - n \cdot Pr \qquad \text{Expression (4)}$$

where b: constant, and
Pr: relative cuff pressure (difference between the cuff pressure at the time when the amplitude of the pulse wave is maximized and each cuff pressure);
a discrimination score calculation section that substitutes the FEI and the FCR ratio of the patient under discrimination into the discrimination function to calculate a discrimination score; and
a diabetes discrimination section that determines whether the patient under discrimination belongs to the healthy group or the diabetes group based on the discrimination score.

10. The finger arterial dilatability testing method according to claim 1, further comprising:
an output step of outputting the calculated index to an output means.

11. The finger arterial dilatability testing device according to claim 4, further comprising:
an output section that outputs the calculated index to an output means.

12. The non-transitory computer-readable recording medium storing the finger arterial dilatability testing program according to claim 7, further comprising:
an output section that outputs the calculated index to an output means.

13. The finger arterial dilatability testing method according to claim 1, wherein the pulse pressure is acquired with a continuous hemomanometer or is estimated from the pulse wave.

14. The finger arterial dilatability testing device according to claim 4, wherein the pulse pressure is acquired with a continuous hemomanometer or is estimated from the pulse wave.

15. The non-transitory computer-readable recording medium storing the finger arterial dilatability testing program according to claim 7, wherein the pulse pressure is acquired with a continuous hemomanometer or is estimated from the pulse wave.

* * * * *